US011248313B2

(12) United States Patent
Omenetto et al.

(10) Patent No.: US 11,248,313 B2
(45) Date of Patent: Feb. 15, 2022

(54) BIOMIMETIC MECHANICAL TENSION DRIVEN FABRICATION OF NANOFIBRILLAR ARCHITECTURE

(71) Applicant: Trustees of Tufts College, Medford, MA (US)

(72) Inventors: Fiorenzo G. Omenetto, Lexington, MA (US); Peter Tseng, Saratoga, CA (US)

(73) Assignee: Trustees of Tufts College, Medford, MA (US)

( * ) Notice: Subject to any disclaimer, the term of this patent is extended or adjusted under 35 U.S.C. 154(b) by 146 days.

(21) Appl. No.: 16/319,468

(22) PCT Filed: Aug. 1, 2017

(86) PCT No.: PCT/US2017/044960
§ 371 (c)(1),
(2) Date: Jan. 21, 2019

(87) PCT Pub. No.: WO2018/026853
PCT Pub. Date: Feb. 8, 2018

(65) Prior Publication Data
US 2019/0292688 A1 Sep. 26, 2019

Related U.S. Application Data

(60) Provisional application No. 62/369,487, filed on Aug. 1, 2016.

(51) Int. Cl.
| | | |
|---|---|---|
| *D01F 4/02* | (2006.01) | |
| *B81C 99/00* | (2010.01) | |
| *B82B 1/00* | (2006.01) | |
| *B82B 3/00* | (2006.01) | |
| *B82Y 30/00* | (2011.01) | |
| *B82Y 40/00* | (2011.01) | |
| *D01F 4/00* | (2006.01) | |
| *A61L 27/22* | (2006.01) | |

(52) U.S. Cl.
CPC .............. *D01F 4/02* (2013.01); *A61L 27/227* (2013.01); *B81C 99/0085* (2013.01); *B82B 1/002* (2013.01); *B82B 3/0023* (2013.01); *B82B 3/0038* (2013.01); *B82Y 30/00* (2013.01); *B82Y 40/00* (2013.01); *D01F 4/00* (2013.01); *A61L 2400/12* (2013.01)

(58) Field of Classification Search
None
See application file for complete search history.

(56) References Cited

U.S. PATENT DOCUMENTS

| | | |
|---|---|---|
| 4,806,355 A | 2/1989 | Goosen |
| 5,015,476 A | 5/1991 | Cochrum |
| 5,093,489 A | 3/1992 | Diamantoglou |
| 5,245,012 A | 9/1993 | Lombari |
| 5,263,992 A | 11/1993 | Guire |
| 5,270,419 A | 12/1993 | Domb |
| 5,576,881 A | 11/1996 | Doerr |
| 5,902,800 A | 5/1999 | Green |
| 5,932,462 A | 8/1999 | Harris |
| 6,127,143 A | 10/2000 | Gunasekaran |
| 6,245,537 B1 | 6/2001 | Williams |
| 6,267,776 B1 | 7/2001 | O'Connell |
| 6,302,848 B1 | 10/2001 | Larson |
| 6,310,188 B1 | 10/2001 | Mukherjee |
| 6,325,810 B1 | 12/2001 | Hamilton |
| 6,337,198 B1 | 1/2002 | Levene |
| 6,372,244 B1 | 4/2002 | Antanavich |
| 6,379,690 B2 | 4/2002 | Blanchard |
| 6,387,413 B1 | 5/2002 | Miyata |
| 6,395,734 B1 | 5/2002 | Tang |
| 8,247,384 B2 | 8/2012 | Green |

(Continued)

FOREIGN PATENT DOCUMENTS

| | | |
|---|---|---|
| WO | 1997008315 | 3/1997 |
| WO | 2004080346 | 9/2004 |

(Continued)

OTHER PUBLICATIONS

Gupta et al., "Patterned Silk Films Cast from Ionic Liquid Solubilized Fibroin as Scaffolds for Cell Growth", Langmuir 23: 1315-1319 (Year: 2007).*
Lai et al., "Aligned Nanofibrillar Collagen Regulates Endothelial Organization and Migration", Regen Med. 7(5): 649-661 (Sep.) (Year : 2012).*
Liu et al., "Dual-factor loaded functional silk fibroin scaffolds for peripheral nerve regeneration with the aid of neovascularization", RSC Adv., 6, 7683. (Year: 2016).*
Schaffner et al., "Structure and Function of RGD Peptides Involved in Bone Biology", Cell Mol Life Sci, Jan. 2003, 60(1), 119-132.
Shi, J., et al. Microcontact Printing and Lithographic Patterning of Electrospun Nanofibers. Langmuir 25, 6015-6018 (2009).
Srinivasan, U., et al. Microstructure to substrate self-assembly using capillary forces. J. Microelectromechanical Syst. 10, 17-24 (2001).
Syms, R. R. A., et al. Surface tension-powered self-assembly of microstructures—the state-of-the-art. J. Microelectromechanical Syst. 12, 387-417 (2003).

(Continued)

*Primary Examiner* — Anand U Desai
(74) *Attorney, Agent, or Firm* — Quarles & Brady, LLP

(57) ABSTRACT

This present disclosure provides methods for utilizing such forces in when generating nanofibrillar constructs with engineered morphology from the nano- to macro-scales. Using for example, a biopolymer silk fibroin as a base material, patterns an intermediate hydrogel were generated within a deformable mold. Subsequently, mechanical tension was introduced via either hydrogel contraction or mold deformation, and finally a material is reentrapped in this transformed shape via beta-sheet crystallization and critical point drying. Topdown engineered anchorages, cables, and shapes act in concert to mediate precision changes in nanofiber alignment/orientation and a macroscale form of provided nanofibrillar structure. An ability of this technique to engineer large gradients of nano- and micro-scale order, manipulate mechanical properties (such as plasticity and thermal transport), and the in-situ generation of 2D and 3D, multi-tiered and doped, nanofibrillar constructs was demonstrated.

11 Claims, 19 Drawing Sheets

(56) References Cited

U.S. PATENT DOCUMENTS

| | | | |
|---|---|---|---|
| 9,925,299 | B2 | 3/2018 | Kaplan |
| 9,925,301 | B2 | 3/2018 | Kaplan |
| 2004/0067503 | A1 | 4/2004 | Tan |
| 2010/0028451 | A1 | 2/2010 | Kaplan |
| 2010/0178304 | A1 | 7/2010 | Wang |
| 2011/0046686 | A1 | 2/2011 | Kaplan |
| 2011/0171239 | A1 | 7/2011 | Kaplan |
| 2014/0058077 | A1 | 2/2014 | Laukkanen |
| 2016/0263228 | A1 | 9/2016 | Kluge |

FOREIGN PATENT DOCUMENTS

| | | |
|---|---|---|
| WO | 2005012606 | 2/2005 |
| WO | 2005123114 | 12/2005 |
| WO | 2007016524 | 2/2007 |
| WO | 2008118133 | 10/2008 |
| WO | 2008150861 | 12/2008 |
| WO | 2011005381 | 1/2011 |
| WO | 2011041395 | 4/2011 |
| WO | 2011109691 | 9/2011 |
| WO | 2011130335 | 10/2011 |
| WO | 2013152265 | 10/2013 |
| WO | 2015070108 | 5/2015 |

OTHER PUBLICATIONS

Takahashi et al., "Induction of Pluripotent Stem Cells from Adult Human Fibroblasts by Defined Factors", Cell, Nov. 30, 2007, 131(5), 861-872.
Takei, F., et al. "Further evidence for importance of the subunit combination of silk fibroin in its efficient secretion from the posterior silk gland cells." The Journal of cell biology 105.1 (1987): 175-180.
Tanaka et al., "Determination of the Site of Disulfide Linkage Between Heavy and Light Chains of Silk Fibroin Produced by Bombyx Mori", Biochim. Biophys. Acta., Jun. 15, 1999, 1432(1), 92-103.
Tanaka et al., "Immunological Identification of the Major Disulfide-Linked Light Component of Silk Fibroin", J. Biochem, Jul. 1993, 114(1), 1-4.
Wang, P., et al. Functionalized polymer nanofibers: a versatile platform for manipulating light at the nanoscale. Light Sci. Appl. 2, e102 (2013).
Wenk et al., "Silk Fibroin Spheres as a Platform for Controlled Drug Delivery", J Control Release, Nov. 24, 2008, 132(1), 26-34.
Wray et. al., "Effect of Processing on Silk-Based Biomaterials: Reproducibility and Biocompatibility", Journal of Biomedical Materials Research Part B: Applied Biomaterials, Jun. 21, 2011, 99, 89-101.
Xu, C. Y., et al. Aligned biodegradable nanofibrous structure: a potential scaffold for blood vessel engineering. Biomaterials 25, 877-886 (2004).
Xu, S. et al. Assembly of micro/nanomaterials into complex, three-dimensional architectures by compressive buckling. Science 347, 154-159 (2015).
Yang, M et al. Ca2+-induced self-assembly of Bombyx mori silk sericin into a nanofibrous network-like protein matrix for directing controlled nucleation of hydroxylapatite nano-needles. J. Mater. Chem. B 3, 2455-2462 (2015).
Yu et al., "Induced Pluripotent Stem Cell Lines Derived from Human Somatic Cells", Dec. 21, 2007, 318(5858), 1917-1920.
Zhang, L., et al. Micro/nanofiber optical sensors. Photonic Sens. 1, 31-42 (2010).
Acharya et al., "Performance Evaluation of a Silk Fibroin Protein-Based Matrix for the Enzymatic Conversion of Tyrosine to L-DOPA", Biotechnol J., Feb. 2008, 3(2), 226-233.
Akiyama, T., et al. Scratch drive actuator with mechanical links for self-assembly of three-dimensional MEMS. J. Microelectromechanical Syst. 6, 10-17 (1997).
Altman et al., "Silk-Based Biomaterials", Biomaterials, Feb. 2003, 24(3), 401-416.
Bayraktar et al., "Silk Fibroin as a Novel Coating Material for Controlled Release of Theophylline", European Journal of Pharmaceutics and Biopharmaceutics, Apr. 1, 2005, 60, 373-381.
Bini, E., et al. "Mapping domain structures in silks from insects and spiders related to protein assembly." Journal of molecular biology 335.1 (2004): 27-40.
Cao, H., et al. The application of nanofibrous scaffolds in neural tissue engineering. Adv. Drug Deliv. Rev. 61, 1055-1064 (2009).
Chen, S. et al. Electrospun carbon fiber mat with layered architecture for anode in microbial fuel cells. Electrochem. Commun. 13,1026-1029 (2011).
Chen, X., et al. Conformation transition kinetics of Bombyx mori silk protein. Proteins 68, 223-231 (2007).
Demura et al, Immobilization of glucose, oxidase with Bombyx mori silk fibroin by only stretching treatment and its application to glucose sensor, 33 Biotech & Biogen. 598 (1989).
Dijke et al., "Growth Factors for Wound Healing", Bio/Technology, 1989, 7, 793-798.
Fernandes, H., et al. An active infrared thermography method for fiber orientation assessment of fiber-reinforced composite materials. Infrared Phys. Technol. 72, 286-292 (2015).
Fuchs, E. et al. "Multiple keratins of cultured human epidermal cells are translated from different mRNA molecules." Cell 17.3 (1979): 573-582.
Gladman, SA, et al. Biomimetic 4D printing. Nat. Mater. 15, 413-418 (2016).
Hahn, M. S. et al. Photolithographic patterning of polyethylene glycol hydrogels. Biomaterials 27, 2519-2524 (2006).
Hanukoglu, I. et al. "The cDNA sequence of a type II cytoskeletal keratin reveals constant and variable structural domains among keratins." Cell 33.3 (1983): 915-924.
Harsh, K. F., et al. Solder self-assembly for three-dimensional microelectromechanical systems. Sens. Actuators Phys. 77, 237-244 (1999).
Hersel et al., "RGD Modified Polymers: Biomaterials for Stimulated Cell Adhesion and Beyond", Biomaterials, Nov. 2003, 24(2), 4385-4415.
Hofmann et al., Silk Fibroin as an Organic Polymer for Controlled Drug Delivery, J Control Release, Mar. 10, 2006, 111(1-2), 219-227.
Hou, H. et al. Electrospun Polyacrylonitrile Nanofibers Containing a High Concentration of Well-Aligned Multiwall Carbon Nanotubes. Chem. Mater. 17, 967-973 (2005).
Hsu, L.-H. et al. Nanofibrous hydrogels self-assembled from naphthalene diimide (NDI)/amino acid conjugates. RSC Adv. 5, 20410-20413 (2015).
Hu et al., "Regulation of Silk Material Structure by Temperature-Controlled Water Vapor Annealing", Biomacromolecules, May 9, 2011, 12, 1686-1696.
Inagaki, M., et al. Carbon Nanofibers Prepared via Electrospinning. Adv. Mater. 24, 2547-2566 (2012).
International Searching Authority, International Search Report and Written Opinion for PCT/US2017/44960, dated Oct. 12, 2017, 7 pages.
Jin et al., "Water-Stable Silk Films with Reduced β-Sheet Content", Advanced Functional Materials, Aug. 2005, 15 (8), 1241-1247.
Kambe, Y., et al. Silk fibroin sponges with cell growth-promoting activity induced by genetically fused basic fibroblast growth factor. J. Biomed. Mater. Res. A 104, 82-93 (2016).
Khang, D.-Y. et al. Molecular Scale Buckling Mechanics in Individual Aligned Single-Wall Carbon Nanotubes on Elastomeric Substrates. Nano Lett. 8, 124-130 (2008).
Kikuchi, Y., et al. "Structure of the Bombyx mori fibroin light-chain-encoding gene: upstream sequence elements common to the light and heavy chain." Gene 110.2 (1992): 151-158.
Kim, S. et al. Silk inverse opals. Nat. Photonics 6, 818-823 (2012).
Kim, U.-J. et al. Structure and properties of silk hydrogels. Biomacromolecules 5, 786-792 (2004).
Li, W.-J., et al. Fabrication and application of nanofibrous scaffolds in tissue engineering. Curr. Protoc. Cell Biol. Editor Board Juan Bonifacino AI Chapter 25, Unit 25.2 (2009).

(56) References Cited

OTHER PUBLICATIONS

Liang, D., et al. Functional electrospun nanofibrous scaffolds for biomedical applications. Adv. Drug Deliv. Rev. 59, 1392-1412 (2007).

Lin, Y. et al. Tuning Chemical and Physical Crosslinks in Silk Electrogels for Morphological Analysis and Mechanical Reinforcement. Biomacromolecules 14, 2629-2635 (2013).

Liu, H., et al. Electrospun Polymer Nanofibers as Subwavelength Optical Waveguides Incorporating Quantum Dots. Small 2, 495-499 (2006).

Liu, X., et al. Nanofibrous hollow microspheres self-assembled from starshaped polymers as injectable cell carriers for knee repair. Nat. Mater. 10, 398-406 (2011).

Lu, S., et al. "Stabilization of enzymes in silk films." Biomacromolecules 10.5 (2009): 1032-1042.

Mandal et al., "High-Strength Silk Protein Scaffolds for Bone Repair", Proceedings of the National Academy of Sciences of the United States of America, May 15, 2012, 109(2), 7699-7704.

Mastrangeli, M. et al. Self-assembly from milli- to nanoscales: methods and applications. J. Micromechanics Microengineering 19, 83001 (2009).

Mitropoulos, A. N. et al. Transparent, Nanostructured Silk Fibroin Hydrogels with Tunable Mechanical Properties. ACS Biomater. Sci. Eng. 1, 964-970 (2015).

Miyairi et al., "Properties of B-Glucosidase Immobilized in Sericin Membrane" 56 J. Fermen. Tech. 303 (1978).

Moll et al., "The Catalog of Human Cytokeratins: Patterns of Expression in Normal Epithelia", Tumors and Cultured Cells, Cell., Nov. 1982, 31(1), 11-24.

Mulder GD, Haberer PA, Jeter KF, eds. Clinicians' Pocket Guide to Chronic Wound Repair. 4th ed. Springhouse, PA: Springhouse Corporation; 1998:85.

Nogueira, G. M. et al. Preparation and characterization of ethanol-treated silk fibroin dense membranes for biomaterials application using waste silk fibers as raw material. Bioresour. Technol. 101, 8446-8451 (2010).

Omenetto et al., "New Opportunities for an Ancient Material", Science, Jul. 30, 2010, 329(5991), 528-531.

Park, M., et al. "Micropatterned stretchable circuit and strain sensor fabricated by lithography on an electrospun nanofiber mat." ACS applied materials & interfaces 5.17 (2013): 8766-8771.

Partlow, B. P. et al. Highly Tunable Elastomeric Silk Biomaterials. Adv. Funct. Mater. 24, 4615-4624 (2014).

Perry, H., et al. Nano- and Micropatterning of Optically Transparent, Mechanically Robust, Biocompatible Silk Fibroin Films. Adv. Mater. 20, 3070-3072 (2008).

Pisignano, D. et al. Polymer nanofibers by soft lithography. Appl. Phys. Lett. 87, 123109 (2005).

Qi, Y. et al. Piezoelectric Ribbons Printed onto Rubber for Flexible Energy Conversion. Nano Lett. 10, 524-528 (2010).

Rockwood, D. N. et al. Materials fabrication from Bombyx mori silk fibroin. Nat. Protoc. 6, 1612-1631 (2011).

Sashina et al., "Structure and Solubility of Natural Silk Fibroin", Russian Journal of Applied Chemistry, Jun. 2006, 79 (6) 869-876.

* cited by examiner

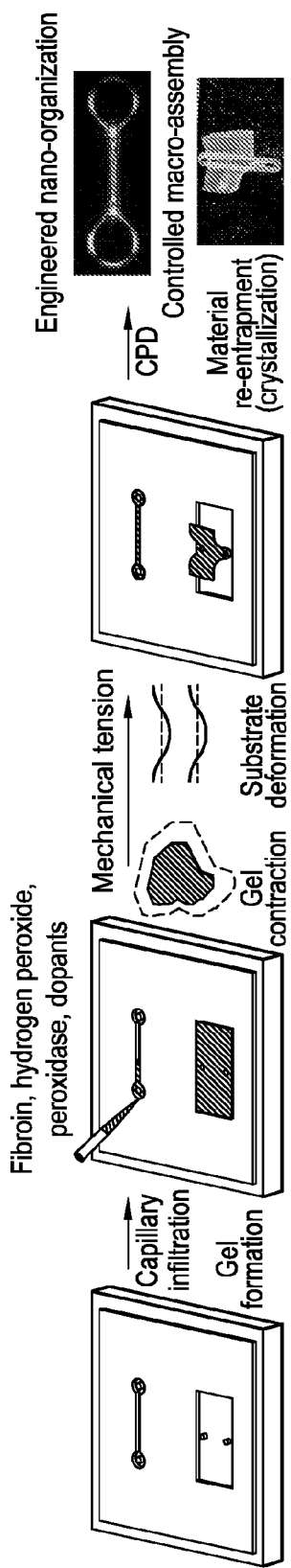
FIG. 1a
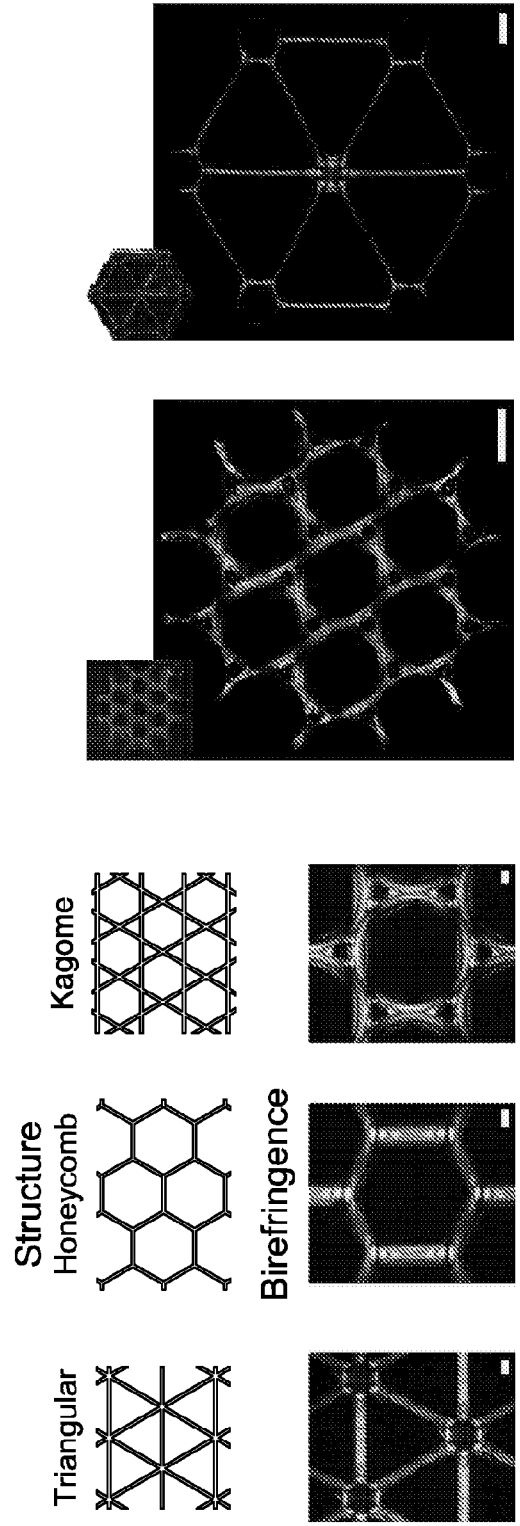
FIG. 1b
FIG. 1c

Increasing birefringence/alignment

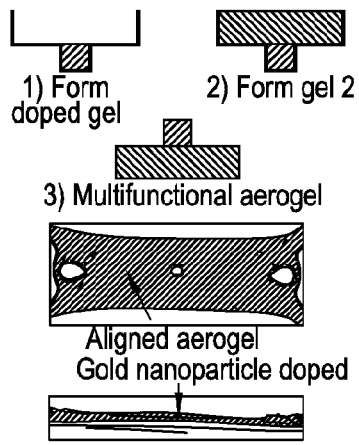
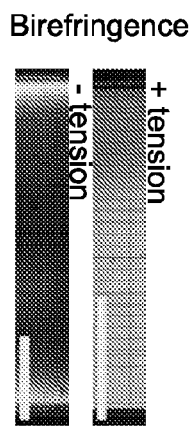
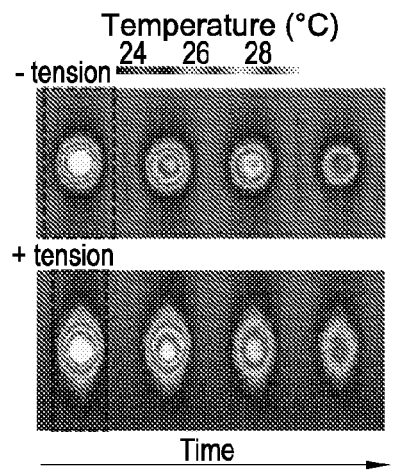
FIG. 4a    FIG. 4b    FIG. 4c
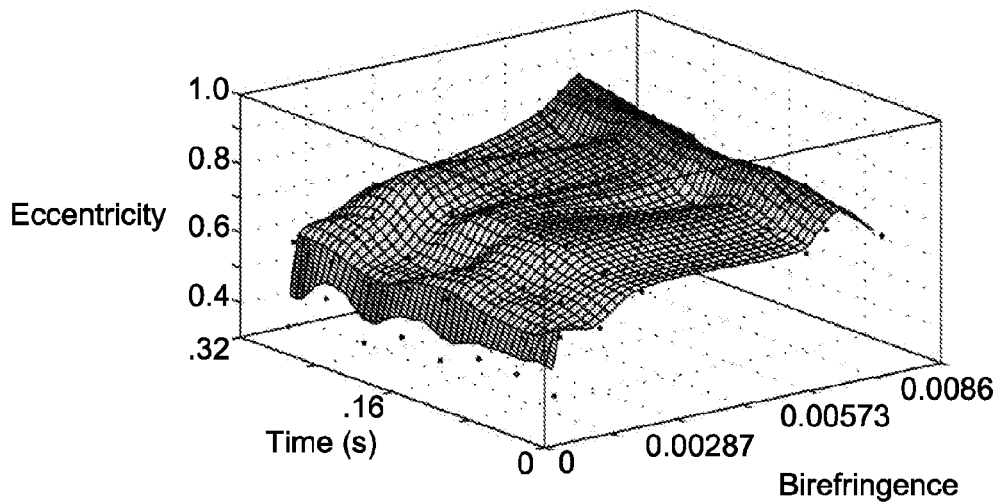
FIG. 4d

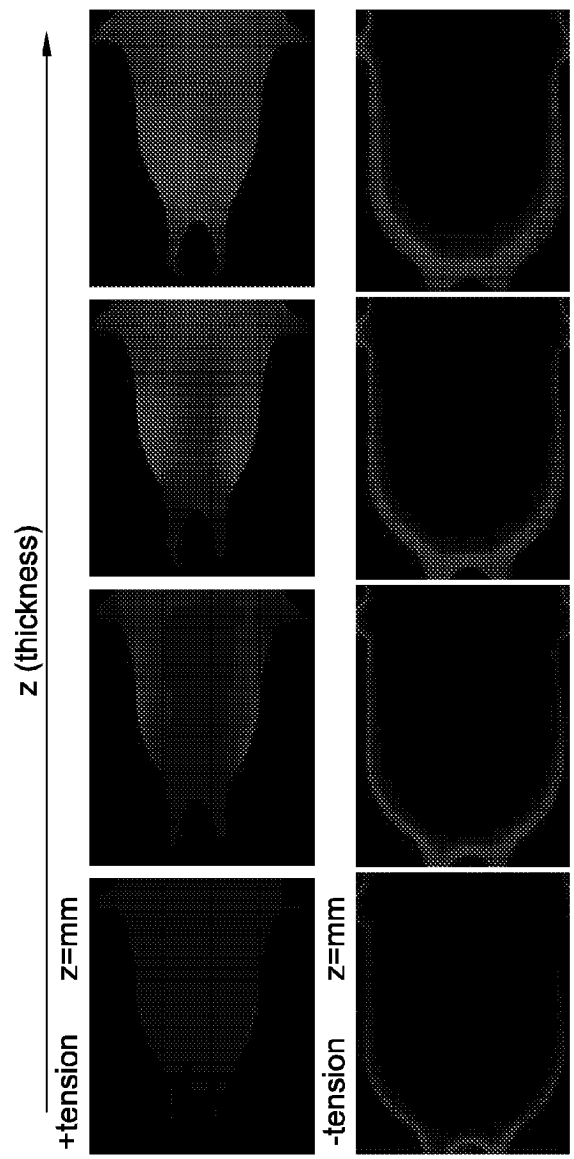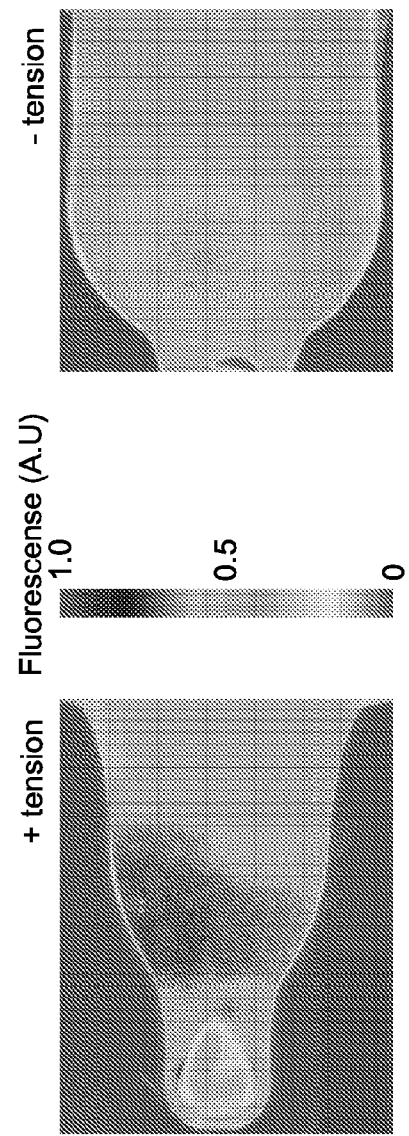
FIG. 12a
FIG. 12b

BIOMIMETIC MECHANICAL TENSION DRIVEN FABRICATION OF NANOFIBRILLAR ARCHITECTURE

CROSS-REFERENCED TO RELATED APPLICATIONS

This application represents the national stage entry of PCT/US2017/044960, filed Aug. 1, 2017, which claims benefit of U.S. Provisional Patent Application 62/369,487 filed Aug. 1, 2016. The contents of these applications are hereby incorporated by reference as set forth in their entirety herein.

GOVERNMENT SUPPORT

This invention was made with government support under grant No. N00014-13-1-0596 awarded by the Office of Naval Research. The government has certain rights in the invention.

BACKGROUND

Naturally-occurring biomaterials, such as extracellular matrix, bone, carapace, and plant fiber possess a porous and oftentimes fibrous structure. Such constructs are readily utilized in nature due to their ability to act as a conduit for materials, chemicals, mechanical forces, and electrical signals while possessing an equivalent strength to their solid counterparts. These transport conduits can be directly facilitated through bulk structure due to its porosity, and additionally across and through individual fibrils in fibrous materials.

Increasingly, fibrous materials in particular have found applications in modern energy, biotechnology, and optical technologies. In biotechnology, for example, such structures are used to mimic the physical characteristics of natural extracellular matrix and have found use in bioassays, in vitro cell culture as a substrate, or as injectables in tissue engineering[1-5]. In energy, for example, fibrous electrodes are becoming increasingly popular due to their high porosity and exposed surface area, thus enabling high power electrocatalytic mats[6-8]. In optics, for example, the nearfield confinement of such fibers are used as waveguides[9-11].

SUMMARY

The present disclosure provides, among other things, articles of manufacture. In some embodiments, articles of manufacture include, for example, nanofibrillar architectures. In some embodiments, the present disclosure provides methods of making and using such architectures.

In some embodiments, nanofibrillar architectures as provided herein include materials and structures that are fibrillar or fibrous. In some embodiments, nanofibrillar architectures include fibrous or fibrillar materials. In some embodiments, nanofibrillar architectures include fibrous or fibrillar proteins. In some nanofibrillar architectures are or include, for example actin, collagen, elastins, keratin, myosin, and/or silk.

In some embodiments, nanofibrillar architectures are semi-crystalline, substantially crystalline, and/or crystalline.

In some embodiments, nanofibrillar architectures as provided include at least one additive, agent, and/or functional moiety. In some embodiments, at least one additive, agent, and/or functional moiety coats an outer surface of a nanofibrillar architecture. In some embodiments, at least one additive, agent, and/or functional moiety permeates throughout (i.e. at least one additive, agent, and/or functional moiety was added to a solution before being infiltrated into a mold).

In some embodiments, nanofibrillar architectures as provided herein are large-scale structures. In some embodiments, nanofibrillar architectures as provided herein are capable of forming large-scale structures. In some embodiments, nanofibrillar architectures, for example are at least on an order of centimeter scale and larger.

In some embodiments, nanofibrillar architectures include nanostructures, microstructures, and/or macrostructures. In some embodiments, nanofibrillar architectures are two dimensional. In some embodiments, nanofibrillar architectures are three dimensional.

In some embodiments, nanofibrillar architectures are shaped and/or form unique structures. In some embodiments, nanofibrillar architectures form structures, including metashapes, for example triangular, hexagonal (honeycomb), and trihexagonal (kagome) cells.

In some embodiments, nanofibrillar architectures exhibit birefringence. In some embodiments, such birefringence corresponds to time and/or stress of compositions or materials when under tension. In some embodiments, birefringence corresponds logarithmically with stress applied in forming nanofibrillar architectures.

In some embodiments, low birefringence ($1^{st}$ order) exhibits relative disorder and minor nanofibril alignment. In some embodiments, increasing birefringence leads first to an emergence of longer fibrils in a span of 15 to 30 degrees from a dominant tension direction. In some embodiments, tension eventually leads to highly aligned fibrils with alignment near exclusively in its dominant tension direction. In some embodiments, high density gels readily formed a thin (typically single layer, <20 nm), porous skin.

In some embodiments, birefringence is characterized by a change in refractive index of a nanofibrillar architecture. In some embodiments, $(\eta_1-\eta_2)$.

In some embodiments, nanofibrils in provided nanofibrillar architectures are substantially aligned in a direction with increased tension. In some embodiments, high density of nanofibrils correlate with pressed fiber sheets. In some embodiments, when nanofibrils of provided nanofibrillar architectures are exposed to tension, such nanofibrils exhibit highly aligned fibrils.

In some embodiments, nanofibrils exposed to higher tension, are characterized by higher density. In some embodiments, nanofibrils in provided nanofibrillar architectures exhibit high density corresponding with a direction of increased tension. In some embodiments, nanofibrils exposed to lower tension, are characterized by lower density.

In some embodiments, the present disclosure provides methods of making nanofibrillar architectures. In some embodiments, methods include programming nanofibrillar architectures.

In some embodiments, provided methods include steps of forming a solution of a fibrillar or fibrous material. In some embodiments, steps include providing a deformable mold. In some embodiments, method steps include infiltrating a solution into a mold. In some embodiments, steps include inducing gelation in a solution. In some embodiments, steps include inducing a mechanical force or tension. In some embodiments, steps include applying a mechanical force or tension to a fibrillar gel to form a nanofibrillar structure. In some embodiments, steps include re-entrapping a nanofibrillar structure to form a nanofibrillar architecture.

In some embodiments, provided methods include forming a solution or providing a solution having a fibrillar or fibrous material. In some embodiments, a solution, for example a silk solution. In some embodiments, a solution is characterized by its concentration and molecular weight. In some embodiments, when a fibrillar or fibrous material is a protein, a solution has a fibrillar or fibrous material concentration between about 1% and 30%. In some embodiments, when a fibrillar or fibrous material is a protein, a solution includes a fibrillar or fibrous material having a molecular weight below 400 kDa.

In some embodiments, a solution includes or further includes at least one additive, agent, and/or functional moiety. In some embodiments, a solution is doped before it is infiltrated into a mold.

In some embodiments, steps include providing a mold. In some embodiments, steps include providing a deformable mold. In some embodiments, a deformable mold is or includes polydimethylsiloxane (PDMS). In some embodiments, a mold includes anchorages, cables, shapes, other structures that are or can be utilized when applying mechanical forces or tensions to a gel.

In some embodiments, steps include infiltrating a solution into a mold. In some embodiments, infiltrating, for example, includes adding or pouring. In some embodiments, when a solution infiltrates a mold, it engages or contacts a mold's anchorages, cables, shapes, other structures.

In some embodiments, steps include inducing gelation in a solution. In some embodiments, gelation forms a pattern conforming with or conforming to a mold. In some embodiments, forming a gel, for example, occurs by any steps known to an ordinarily skill artisan. In some embodiments, forming a gel occurs via capillary infiltration and gelation. In some embodiments, for example when a solution is a silk solution, gelation occurs for example by mixing silk solutions with acetone and ultrasonic agitation, mixing silk solutions with peroxide/peroxidase combination.

In some embodiments, inducing or applying a mechanical force or tension to a fibrillar gel to form a nanofibrillar structure, includes introduced by hydrogel contraction or mold deformation.

In some embodiments, a step of applying a mechanical force or tension to a fibrillar gel includes a step of hydrogel contraction, for example, includes submersion of a hydrogel in a mixture of water and ethanol. In some embodiments, a mixture of water and ethanol is between about 0% ethanol and 50% ethanol.

In some embodiments, a step of applying a mechanical force or tension to a fibrillar gel includes a step of mold deformation, for example direct deformation of a deformable mold.

In some embodiments, steps include re-entrapping a nanofibrillar structure to form a nanofibrillar architecture. In some embodiments, a tensed/biased nanofibrillar structure is then re-entrapped in its state via a crystallization step, for example via inducing beta-sheet crystallization. Beta-sheet formation can occur or be induced via any mode known to an ordinarily skilled artisan.

In some embodiments, resultant nanofibrillar architectures are characterized by their homogeneous or heterogenous composition. In some embodiments, resultant nanofibrillar architectures are characterized by their birefringence. In some embodiments, resultant nanofibrillar architectures are characterized by their directional stresses. In some embodiments, resultant nanofibrillar architectures are characterized by their two dimensional and three dimensional metashapes.

In some embodiments, nanofibrillar architectures as provided herein are made from or manufactured by methods as provided herein.

BRIEF DESCRIPTION OF THE DRAWING

The foregoing and other objects, aspects, features, and advantages of the present disclosure will become more apparent and better understood by referring to the following description taken in conjunction with the accompanying figures in which:

FIG. 1 shows mechanical tension-mediated formation of patterned nanofibrillar structure. FIG. 1 at panel (a) shows a general schematic of a protocol as provided herein. Aqueous silk fibroin is mixed with cross-linkers hydrogen peroxide and horseradish peroxidase (alongside optional dopants), and infiltrated/gelled in a PDMS mold. Mechanical tension is subsequently introduced via either contraction of the gel in mixtures of ethanol and water, or direct deformation of the elastomeric substrate. Material is subsequently re-entrapped in its tensed state (via beta-sheet crystallization) and transformed into an aerated structure using critical point drying. Final structure possesses tension-engineered nano-, micro-, and macrostructure. FIG. 1 at panel (b) shows birefringence of sample micro-scale, nanofibrillar unit cells generated from periodic metashapes (triangular, hexagonal, and tri-hexagonal). Scale bars, 100 μm. FIG. 1 at panel (c) shows large scale metastructures composed of tri-hexagonal and triangular components. Scale bars, 1 mm.

FIG. 2 at panel (a) shows birefringence and 2d simulation (nonlinear mechanical analysis in Comsol Multiphysics) of stress distribution in fibers anchored via rings spaced by 250 μm, 1125 μm, and 3125 μm and contracted by 33%. Longer distances results in a large peak stress and an accompanying higher birefringence. Imaged birefringence of provided porous structures typically peaked at third order colors. Scale bar, 200 μm. FIG. 2 at panel (b) shows scanned-electron-microscopy of provided aligned nanofibrillar structures at low and high fibril density. At high densities provided structures exhibit an appearance of a stacked set of fibers. FIG. 2 at panel (c) shows birefringence and corresponding internal nanofibrillar morphology of provided typical nanofibrillar structure. Increasing stress and birefringence correspond to increasing fiber alignment and orientation. Scale bars for SEM images are 200 nm. FIG. 2 at panel (d) and FIG. 2 at panel (e) show engineerable silk hydrogel contraction in mixtures of ethanol and water, and corresponding birefringence of ring junction structures at increasing contraction. N=3. FIG. 2 at panel (f) shows a schematic of a design to generate tensed and untensed fibers for mechanical characterization and corresponding birefringence. FIG. 2 at panel (g) shows an average increase in mechanical strength of tensed fibers (plotted with standard error), indicative of strain-stiffening that occurs in silk hydrogels that translates to the dry, porous structure. N=4 for each set.

FIG. 3 at panel (a) and FIG. 3 at panel (b) show an effect of spaced anchorages in reshaping a cylindrical particle. 2-spaced anchorages result in an elliptic cylinder, while 4-spaced anchorages result in a concave square. FIG. 3 at panel (b) shows heterogenous surface morphology of a porous, contracted elliptic cylinder (>50%, formed from 1.0% silk fibroin). Nanofiber orientation and density shift across the structure as a result of generated stress. FIG. 3 at panel (c) shows Comsol-simulated stress, birefringence, and fluorescence of fluorescent nanoparticle-doped elliptic cylinders of increasing eccentricity contracted by 33%. Initiation of contraction yields a correspondingly asymmetric stress, birefringence, and nanoparticle doping. FIG. 3 at panel (d) shows methods of fabricating 3-dimensional nanofibrillar structures. Buckling instabilities can be induced via either design of anchorages during gel contraction or the swelling of aerated high-aspect-ratio aligned beams in ambient humidity. 3-d structures can additionally be induced directly via deformation of the PDMS substrate. FIG. 3 at panel (e) shows 3-d nonlinear mechanical simulation of anchorage-induced buckling instabilities induced via 90 degree anchorages, and corresponding pop-up morphology of a 3-d spire-type structure induced via increasing tensile stress. FIG. 3 at panel (e) shows simulation and corresponding pop-up morphology of thin plates pulled by 2 and 3 anchorages. FIG. 3 at panel (f) shows buckling of high-aspect-ratio beams with increasing birefringence/alignment of fibers. Generally, alignment and aspect-ratio are correlated with ambient moisture swelling and pop-up height. FIG. 3 at panel (g) shows transformation of pop-up nanofibrillar structures at high humidity. Increasing inculcation of water plasticizes silk fibroin, reducing its elastic modulus and increasing flexibility, thus causing structural collapse. FIG. 3 at panel (h) shows transformation of pop-up structure height over time at 75 and 95% humidity, plotted with standard error (N=2 at each humidity).

FIG. 4 at panel (a) shows a multi-tiered nanofibrillar structure composed of undoped and doped portions of aerogel formed via sequential infiltration and gelation steps. FIG. 4 at panel (b) and FIG. 4 at panel (c) show birefringence and corresponding infrared thermography of tensed and untensed multi-tiered test structures with a small plasmonic heater. Scale bars, 100 μm. Induction of tension leads to a notable change in the temperature distribution across the nanofibrillar structure, namely an eccentric thermal distribution and the appearance of a high temperature "tail" in the direction of nanofibrillar alignment. FIG. 4 at panel (d) shows a plot of thermal distribution eccentricity as a function of time and structure birefringence. FIG. 4 at panel (e) and FIG. 4 at panel (f) show a large structural web (2 cm width) and corresponding birefringence of the structure. FIG. 4 at panel (g) shows 6-anchorage nanofibrillar web (~2.5 mg) supporting a 0.11 N point load (11 g). Scale bar: 500 μm.

FIG. 5 at panel (a) shows from a top down. FIG. 5 at panel (b) shows from an edge.

FIG. 8 at panel (a) shows denser, porous "skin" on the surface, and looser interior structure of a nanofibrillar construct formed from 4% silk fibroin.

FIG. 8 at panel (b) shows establishing zones with distinct nanomorphologies in a single structure. Scanning electron microscopy images of the surface of constrained and unconstrained (by anchorage) regions reveals the nanofibrillar alignment and orientation varies with position. Alignment vector is computed via FibrilTool in ImageJ.

FIG. 12 shows materials under tension. FIG. 12 at panel (a) shows confocal z-steps of provided elliptic cylinder test structures with and without induced mechanical tension. Untensed structures display a cup-like morphology, whereas tensed structures display slightly higher thicknesses at regions of high tension. FIG. 12 at panel (b) shows maximum fluorescence of tensed and untensed structures. Fluorescent nanoparticles distribute at higher densities to regions of higher tension.

FIG. 13 at panel (a) shows an appearance of gold-nanoparticle-doped microparticles with and without contraction. FIG. 13 at panel (b) shows heating of gold-nanoparticle-doped nanofibrillar particles. Contraction of the structure leads to a higher plasmon-resonance-induced thermal power output from the doped structures. Each point represents an N=3 or 4.

FIG. 14 at panel (a) shows deformation of a PDMS mold before ethanol extraction and critical point drying entraps provided structures (in this case a wavy fiber) in a new 3d shape. FIG. 14 at panel (b) shows an appearance of provided pop-up test structures before and after exposure to 95% humidity. Excess introduction of moisture plasticizes provided structures. Note, that provided devices retain a blueish color of an aerogel before and after this exposure.

DEFINITIONS

Figure 2A:
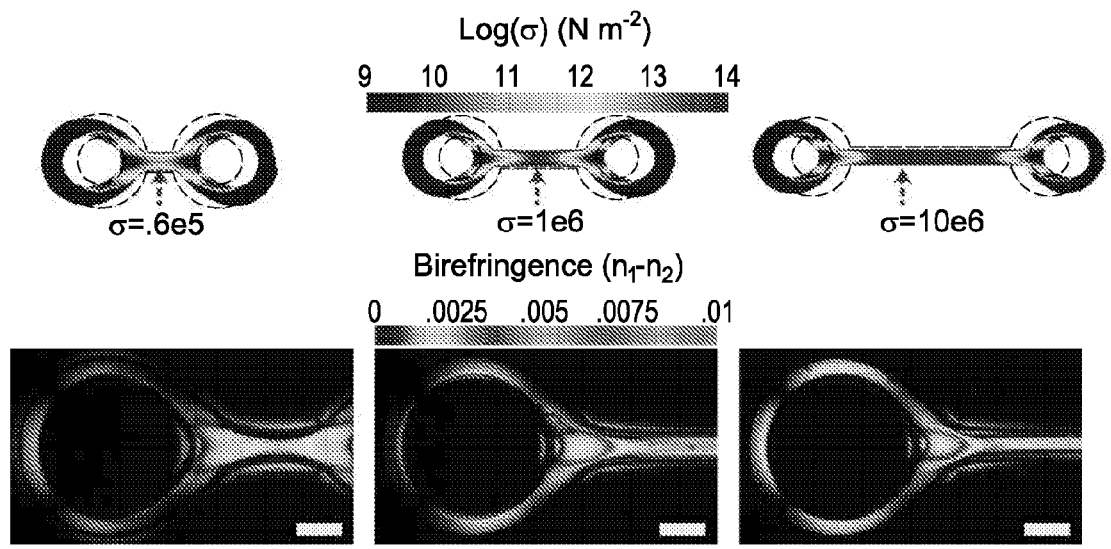
FIG. 2 shows engineering nanofibrillar order.
Figure 2B:
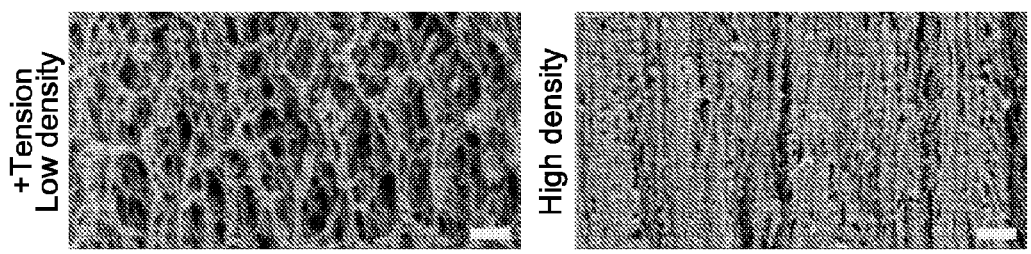
Figure 2C:
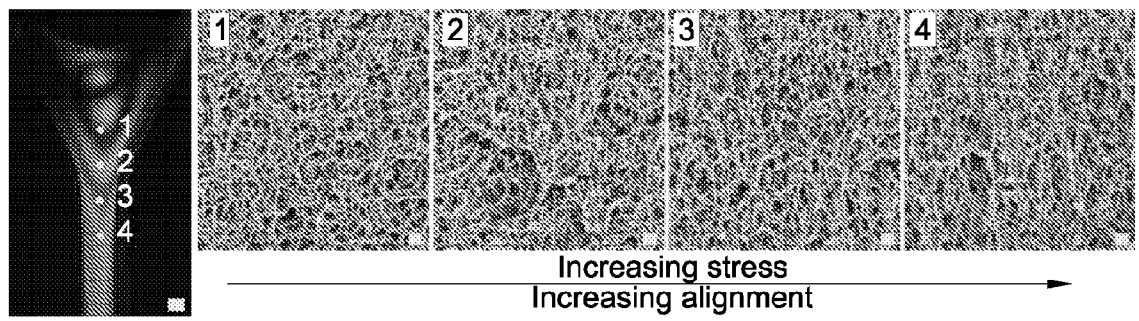
Figure 2D:
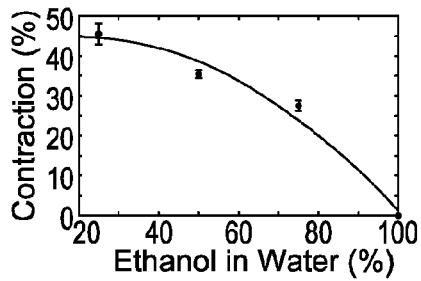
Figure 2E:
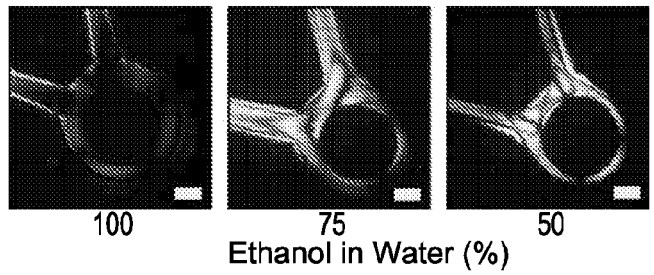
Figure 2F:
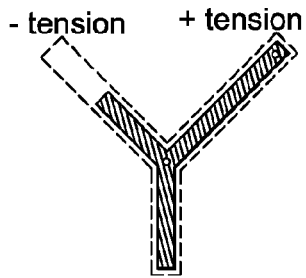
Figure 2G:
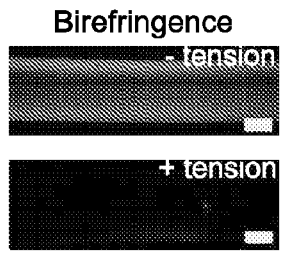
Figure 2G:
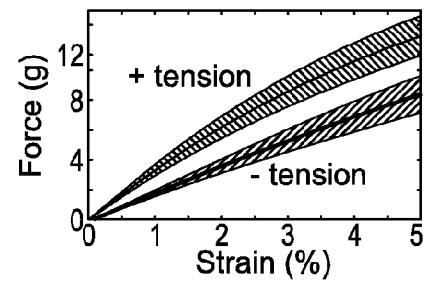
Figure 3A:
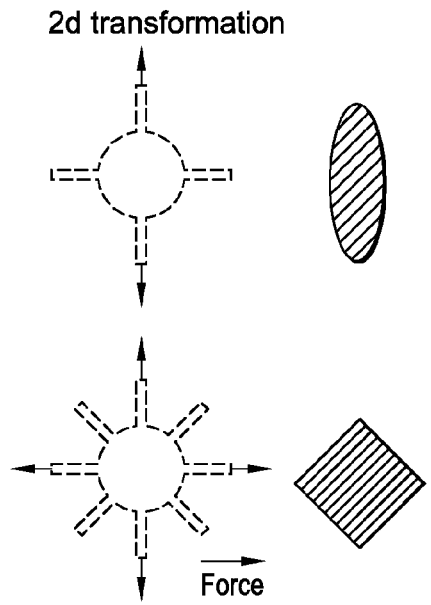
FIG. 3 shows a transformation of nanofibrillar shapes in 2d and 3d.
Figure 3B:
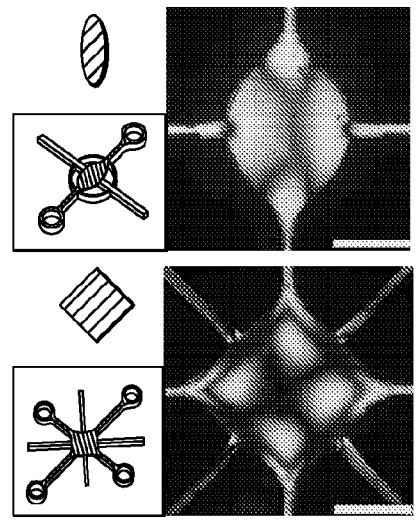
Figure 3C:
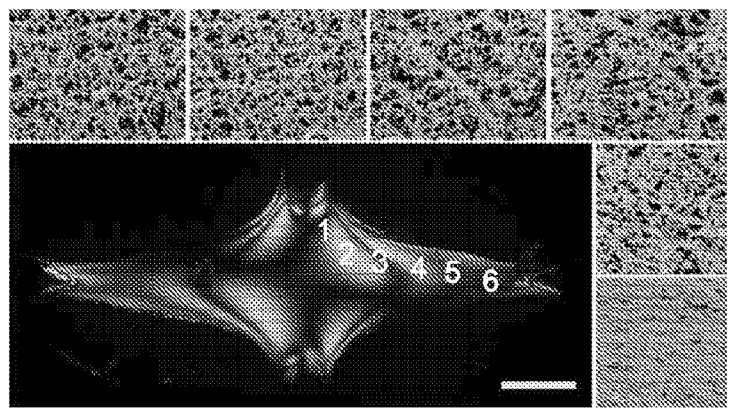
Figure 3D:
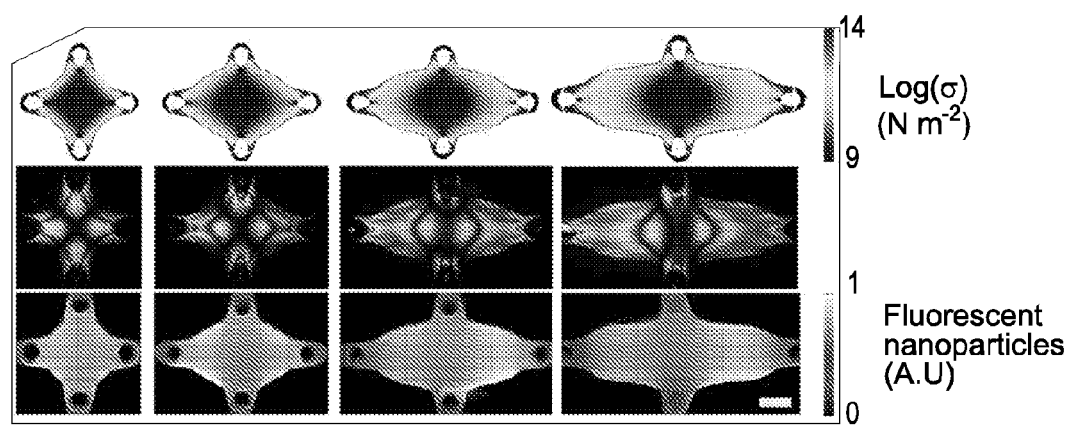
Figure 3D:
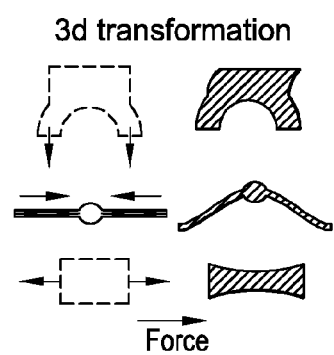
Figure 3E:
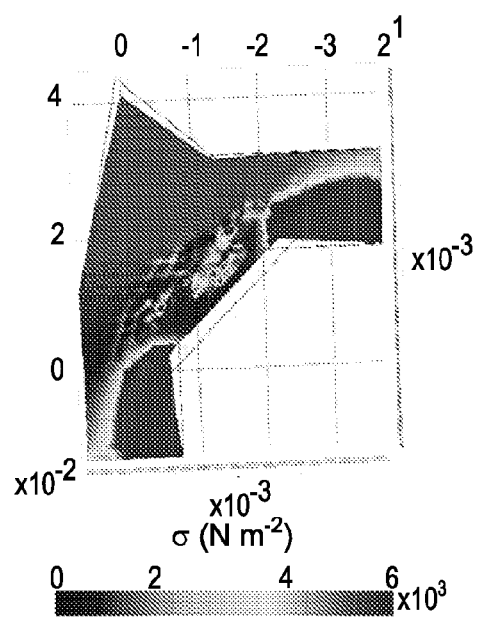
Figure 3E:
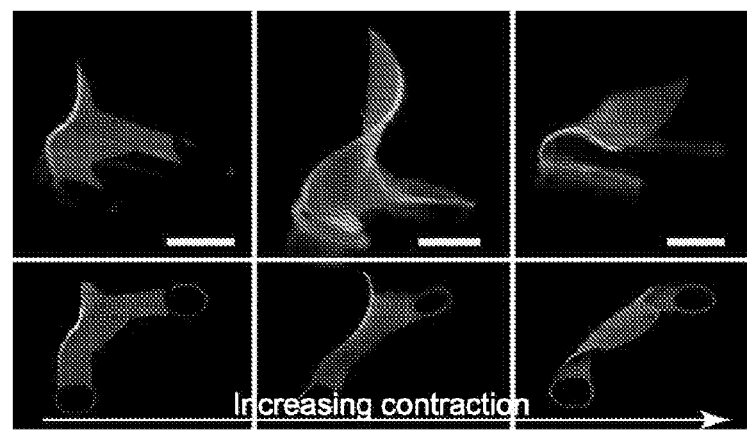
Figure 3F:
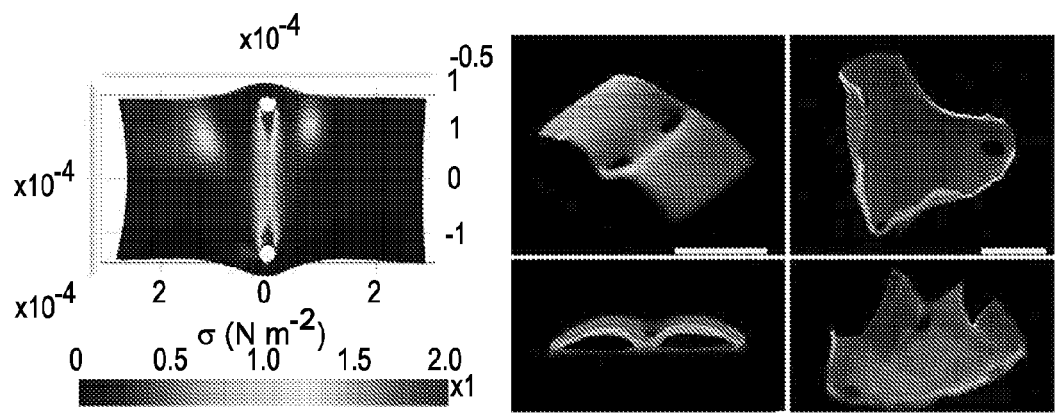
Figure 3F:
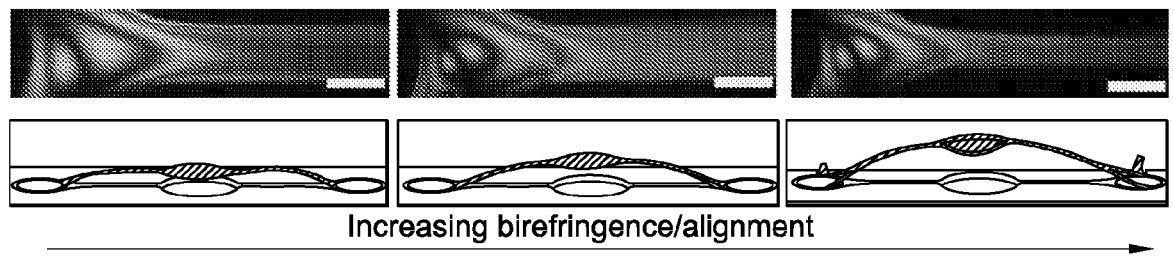
Figure 3G:
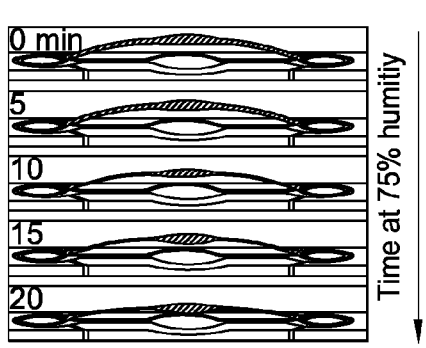
Figure 3H:
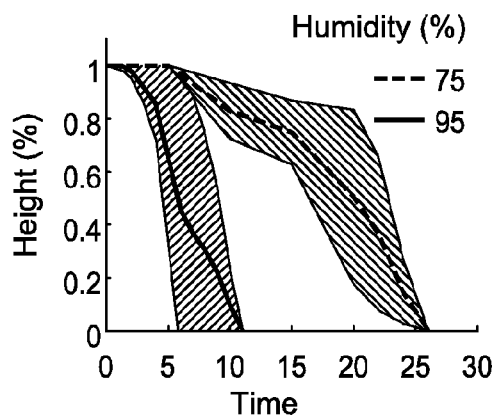

In order for the present disclosure to be more readily understood, certain terms are first defined below. Additional definitions for the following terms and other terms are set forth throughout the specification.

The present specification describes certain inventions relating to so-called "three-dimensional (3D) printing", which can be distinguished from "two-dimensional (2D) printing" in that, the printed product has significant mass in three dimensions (i.e., has length, width, and height) and/or significant volume. By contrast, 2D printing generates printed products (e.g., droplets, sheets, layers) that, although rigorously three-dimensional in that they exist in three-dimensional space, are characterized in that one dimension is significantly small as compared with the other two. By analogy, those skilled in the art will appreciate that an article with dimensions of a piece of paper could reasonably be considered to be a "2D" article relative to a wooden block (e.g., a 2×4×2 block of wood), which would be considered a "3D" article. Those of ordinary skill will therefore readily appreciate the distinction between 2D printing and 3D printing, as those terms are used herein. In many embodiments, 3D printing is achieved through multiple applications of certain 2D printing technologies, having appropriate components and attributes as described herein.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example: streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible:" As used herein, the term "biocompatible" is intended to describe any material which does not elicit a substantial detrimental response in vivo.

"Biodegradable": As used herein, the term "biodegradable" is used to refer to materials that, when introduced into cells, are broken down by cellular machinery (e.g., enzymatic degradation) or by hydrolysis into components that cells can either reuse or dispose of without significant toxic effect(s) on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component and/or into fragments thereof (e.g., into monomeric or submonomeric species). In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid) (PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Comparable": As used herein, the term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," "attached," and "associated with," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used. Typically the moieties are attached either by one or more covalent bonds or by a mechanism that involves specific binding. Alternately, a sufficient number of weaker interactions can provide sufficient stability for moieties to remain physically associated.

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Hygroscopic": As used herein, the term "hygroscopic"

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

The term "polypeptide", as used herein, generally has its art-recognized meaning of a polymer of at least three amino acids, linked to one another by peptide bonds. In some embodiments, the term is used to refer to specific functional classes of polypeptides. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. Alternatively or additionally, in many embodiments, such member also shares a particular characteristic sequence element with the reference polypeptide (and/or with other polypeptides within the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. In some embodiments, a polypeptide may comprise natural amino acids, non-natural amino acids, or both. In some embodiments, a polypeptide may comprise only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups, e.g., modifying or attached to one or more amino acid side chains, and/or at the polypeptide's N-terminus, the polypeptide's C-terminus, or both. In some embodiments, a polypeptide may be cyclic. In some embodiments, a polypeptide is not cyclic. In some embodiments, a polypeptide is linear.

"Stable": As used herein, the term "stable," when applied to compositions means that the compositions maintain one or more aspects of their physical structure and/or activity over a period of time under a designated set of conditions. In some embodiments, the period of time is at least about one hour; in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37 degrees Celsius for example in serum or in phosphate buffered saline). In some embodiments, the designated conditions are under cold storage (e.g., at or below about 4 degrees Celsius, –20 degrees Celsius, or –70 degrees Celsius). In some embodiments, the designated conditions are in the dark.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Substantially free" As used herein, the term "substantially free" means that it is absent or present at a concentration below detection measured by a selected art-accepted means, or otherwise is present at a level that those skilled in the art would consider to be negligible in the relevant context.

"Sustained release": As used herein, the term "sustained release" and in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%.

DETAILED DESCRIPTION OF CERTAIN EMBODIMENTS

In order to provide some specific examples of certain embodiments of the present disclosure, below are described several exemplary embodiments of provided methods and compositions.

In natural systems, mechanical forces are regularly used to manipulate structural form and function during biological growth and development. These manipulations occur at multiple length scales, including from morphing of a single protein to folding of entire organs.

The present disclosure encompasses a recognition that mechanical forces are utilized in shaping engineered systems. In natural systems, mechanical forces are utilized in-situ to build structures and/or reshape/transform an existing structure. In engineered systems, mechanical forces (through instabilities commonly driven by stress, electromagnetics, and surface tension) have been used to program device orientation, shape, function, and mechanics[18-26].

Fabrication of fibrous structures typically consists of electrospinning (whereby individual fibers are spun and subsequently aligned or woven)[3,7,11], chemical self-assembly[4,12,13], or lithographical formation[14-17]. In general, each of these methods possesses limitations in either the speed of formation, throughput of technique, or the control in fiber orientation and resolution.

In some embodiments, the present disclosure provides articles of manufacture. In some embodiments, provided articles are nanofibrillar architectures. In some embodiments, the present disclosure provides methods of making and using such architectures.

Methods of Making Nanofibrillar Architectures

In some embodiments, the present disclosure provides methods of making nanofibrillar architectures. In some embodiments, methods include programming nanofibrillar architectures. In some embodiments, forming nanofibrillar architectures integrates concepts of engineering from both bottom-up and top-down fabrication.

In some embodiments, provided methods include steps of forming a solution of a fibrillar or fibrous material. In some embodiments, steps include providing a mold. In some embodiments, method steps include infiltrating a solution into a mold. In some embodiments, steps include inducing gelation in a solution. In some embodiments, steps include inducing a mechanical force or tension. In some embodiments, steps include applying a mechanical force or tension to a fibrillar gel to form a nanofibrillar structure. In some embodiments, steps include re-entrapping a nanofibrillar structure to form a nanofibrillar architecture.

In some embodiments, methods include forming a solution or providing a solution of a fibrillar or fibrous material. In some embodiments, a solution, for example a silk solution is characterized by its concentration and molecular weight. In some embodiments, silk hydrogel solutions, composed of fibroin in a range of about 1% to about 30% were utilized.

In some embodiments, a solution includes or further includes at least one additive, agent, and/or functional moiety. In some embodiments, a solution is doped before it is infiltrated into a mold.

In some embodiments, steps include providing a mold. In some embodiments, steps include providing a deformable mold. In some embodiments, a deformable mold is or includes polydimethylsiloxane (PDMS). In some embodiments, forming nanofibrillar architectures, includes providing a mold having micro-definition of anchorages, cables, and interconnects therein. In some embodiments, a mold includes anchorages, cables, shapes, other structures that are or can be utilized when applying mechanical forces or tensions to a gel.

In some embodiments, thick patterns were formed (e.g. 150 to 500 um) for example in SU-8 via photolithography, and replica molded into polydimethylsiloxane (PDMS).

In some embodiments, steps include infiltrating a solution into a mold. In some embodiments, infiltrating, for example, includes adding or pouring. In some embodiments, when a solution infiltrates a mold, it engages or contacts a mold's anchorages, cables, shapes, other structures.

In some embodiments, forming nanofibrillar architectures, includes forming a gel-intermediary through capillary infiltration and gelation. In some embodiments, steps include inducing gelation in a solution. In some embodiments, gelation forms a pattern conforming with or conforming to a mold. In some embodiments, forming a gel, for example, occurs by any steps known to an ordinarily skill artisan. In some embodiments, forming a gel occurs via capillary infiltration and gelation. In some embodiments strategies for generating a silk hydrogel, include mixing silk solutions with acetone and ultrasonic agitation. In some embodiments, solvent-induced hydrogels were found to be problematic due to rapid evaporation of solvent leading to weakly adhered hydrogels, while hydrogels based on coagulation tended to form an inhomogeneous structure. In some embodiments, crosslinked hydrogels formed from the peroxide/peroxidase combination yielded a soft structure (~5 to 100 kPa) with a low initial percentage of beta-sheet and alpha-helix conformational states to serve as a beneficial intermediary structure[29]. In some embodiments, a silk solutions, having fibroin in a range of about 0.5% to about 8% with crosslinkers composed of hydrogen peroxide and horseradish peroxidase were subsequently infiltrated into generated patterns and gelled over 6 hours to form an intermediary, unbiased hydrogel. Generally and unless otherwise noted where a structure was generated using a different concentration, for exemplary experiments a 3% silk fibroin solution was used.

In some embodiments, forming nanofibrillar architectures, includes inducing a mechanical force or tension. In some embodiments, inducing or applying a mechanical force or tension to a fibrillar gel to form a nanofibrillar structure, includes introduced by hydrogel contraction or mold deformation.

In some embodiments, a step of applying a mechanical force or tension to a fibrillar gel includes a step of hydrogel contraction, for example, includes submersion of a hydrogel in a mixture of water and ethanol. In some embodiments, a mixture of water and ethanol is between about 0% ethanol and 50% ethanol.

In some embodiments, a step of applying a mechanical force or tension to a fibrillar gel includes a step of mold deformation, for example direct deformation of a deformable mold.

In some embodiments, a mechanical force or tension on anchored beams generated ordered and aligned nanofibrils. In some embodiments, engineered forces on particles and plates mediated controlled transformations of x, y, and z-dimensional shape, structure, and alignment, ultimately leading to heterogeneous and asymmetric material properties.

In some embodiments, forming nanofibrillar architectures, includes nanofibrillar material re-entrapping. In some embodiments, steps include re-entrapping a nanofibrillar structure to form a nanofibrillar architecture. In some embodiments, a tensed/biased nanofibrillar structure is then re-entrapped in its state via a crystallization step, for example via inducing beta-sheet crystallization. In some embodiments, following application of mechanical force or tension is followed by extraction of water in ethanol. In some embodiments, substrates were critical-point-dried to yield final nanofibrillar architectures. In some embodiments, ethanol and subsequent steps of critical-point-drying induce beta-sheet conformation changes to silk fibroin in an intermediary hydrogel[33-36], restabilizing it in its new state. Beta-sheet formation can occur or be induced via any mode known to an ordinarily skilled artisan.

In some embodiments, resultant nanofibrillar architectures are characterized by their homogeneous or heterogenous composition. In some embodiments, resultant nanofibrillar architectures are characterized by their birefringence. In some embodiments, resultant nanofibrillar architectures are characterized by their directional stresses. In some embodiments, resultant nanofibrillar architectures are characterized by their two dimensional and three dimensional metashapes.

Nanofibrillar Architectures

The present disclosure, in some embodiments, provides engineering of asymmetric mechanical properties via nanoscale alignment. In some embodiments, nanofibrillar architectures have tunable mechanical properties.

In some embodiments, the present disclosure provides large gradients of nano- and micro-scale order. In some embodiments, the present disclosure provides designable gradients via controlled tension. In some embodiments, application of controlled mechanical boundary conditions was found to mediate changes in a structure, shape, and behavior of nanofibrillar architectures, solutions, materials, and/or structures. In some embodiments, methods include mechanical programming of nanofibrillar architectures. In some embodiments, programming nanofibrillar architecture includes manipulating forces and tensions to control structures to form architectures having multiple length scales in a range spanning nanoscale, microscale and macroscale.

In some embodiments, nanofibrillar architectures as provided herein include materials and structures that are fibrillar or fibrous. In some embodiments, nanofibrillar architectures include fibrous or fibrillar proteins. In some nanofibrillar architectures are or include, for example actin, collagen, elastins, keratin, myosin, and/or silk.

In some embodiments, useful polymers include biopolymers. In some embodiments, a useful biopolymer, for example, is or includes silk fibroin. In some embodiments, silk fibroin was utilized.

Silk fibroin protein exists in three conformational states, being random coil (soluble and amorphous), to beta sheet and alpha helix (ordered). In some embodiments, silk can be uniquely and straightforwardly steered from disordered into ordered states via solvent, water vapor, and shear. In some embodiments, silk and it properties allow for it to re-stabilize and entrap provided tensed nanofibrillar structures in its biased state. In some embodiments, silk fibroin is versatile biomaterial with numerous applications in modern nanotechnology, biotechnology, energy, and more. Silk versatility has led to a myriad of material constructs (films, sponges, hydrogels, and particles) possessing tunable mechanical and solubility properties[27-32].

In some embodiments, nanofibrillar architectures are semi-crystalline, substantially crystalline, and/or crystalline.

In some embodiments, nanofibrillar architectures as provided include at least one additive, agent, and/or functional moiety. In some embodiments, at least one additive, agent, and/or functional moiety coats an outer surface of a nanofibrillar architecture. In some embodiments, at least one additive, agent, and/or functional moiety permeates throughout (i.e. at least one additive, agent, and/or functional moiety was added to a solution before being infiltrated into a mold).

Figure 9:
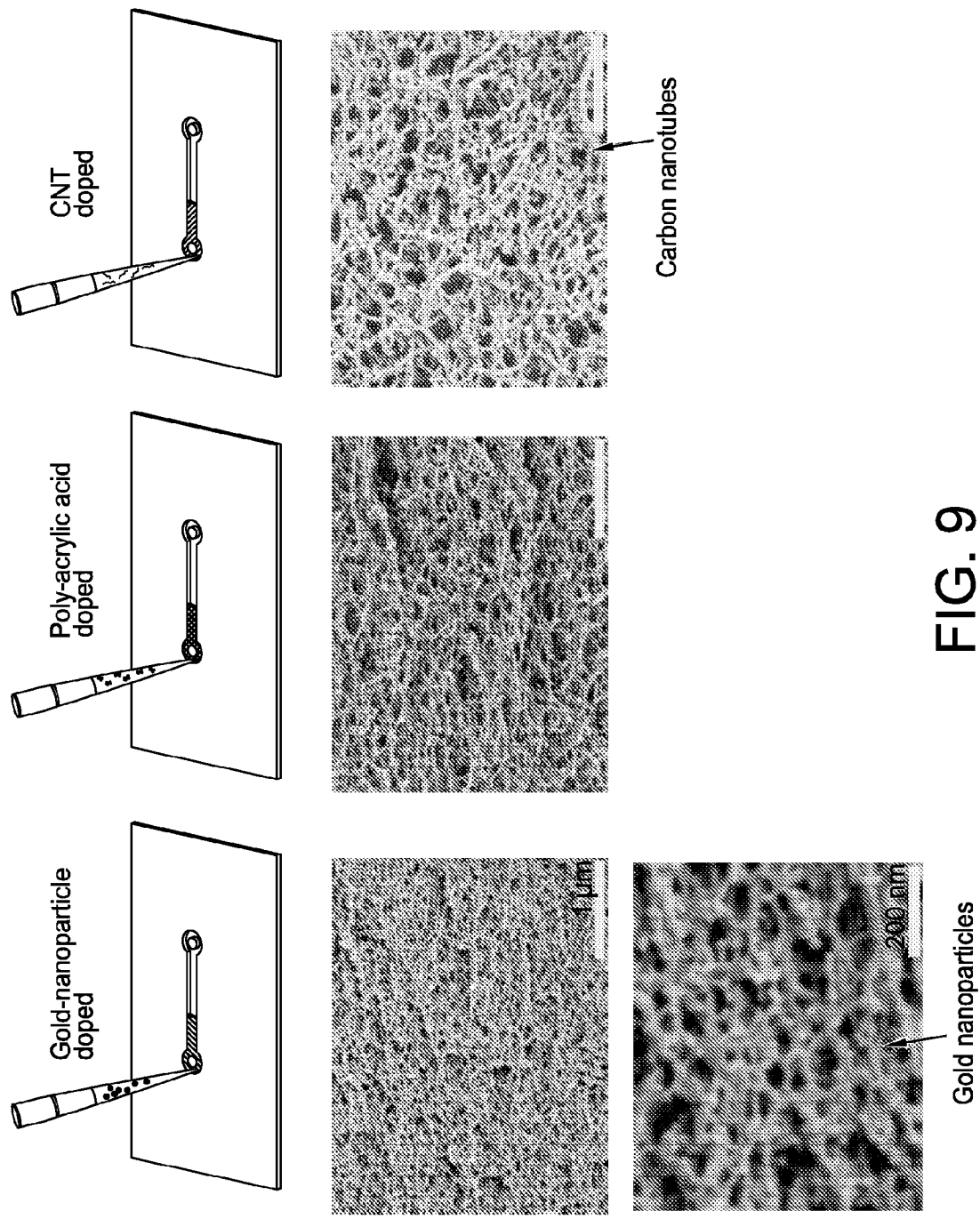
FIG. 9 shows nanomorphology of aligned nanofibrillar structures doped with gold plasmonic nanoparticles, hydrophilic poly-acrylic acid (MW:75 kDa), or carbon nanotubes. Induced mechanical tension forces these dopants into alignment along with the primary silk structure.

In some embodiments, a presence of dopants did not affect generating nanofiber alignment. In some embodiments, gold nanoparticles, polyacylic acid polymer, and carbon nanotubes were found forced into alignment alongside primary nanofibers as shown in FIG. 9.

Figure 7:
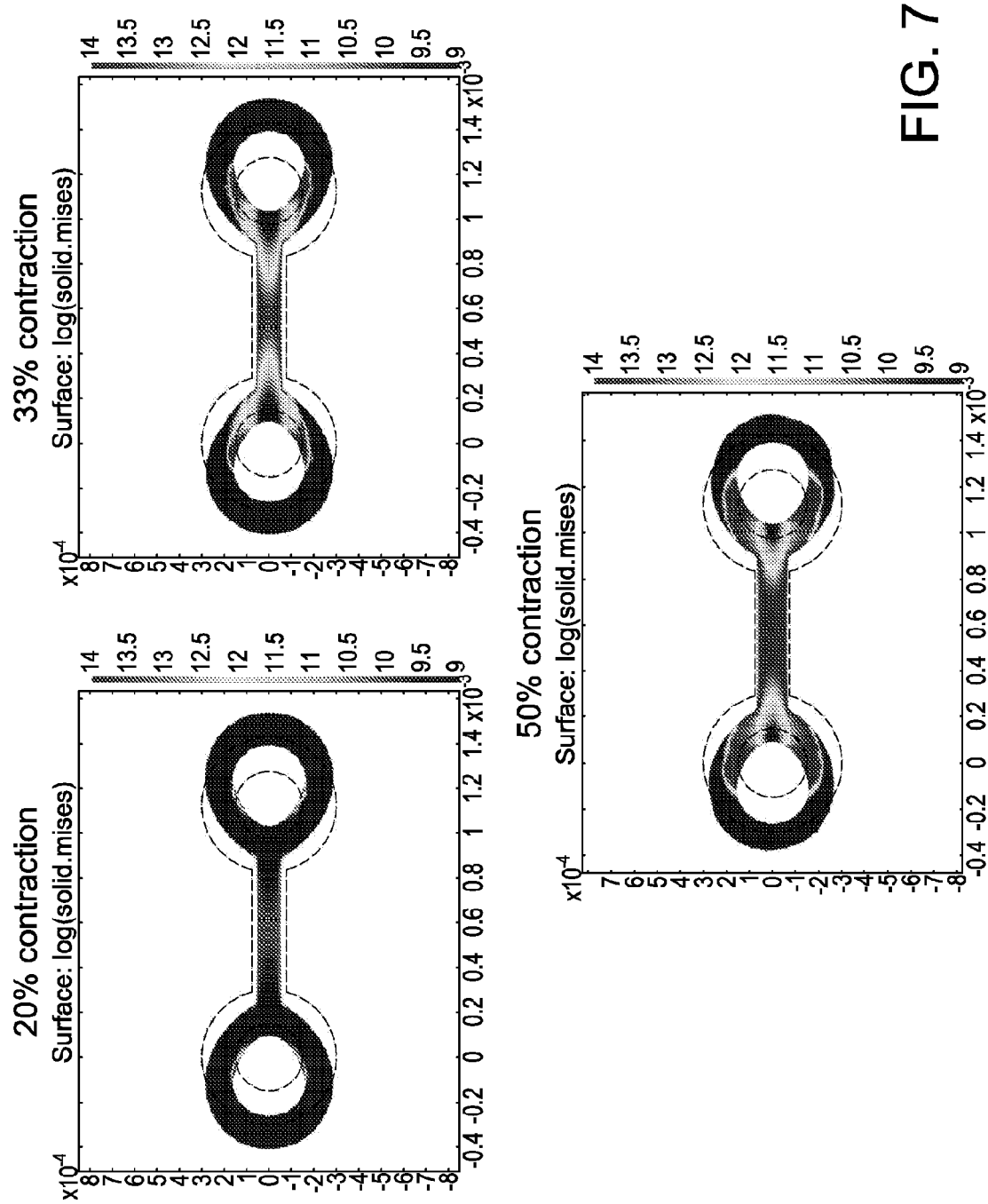
FIG. 7 shows simulated stress on a ring-anchored fiber at 20, 33, and 50% contraction. Increasing contraction leads to increasing maximum stress.

In some embodiments, forming nanofibrillar architectures, includes inducing a mechanical force or tension for example inducing hydrogel contraction or mold deformation. In some embodiments, contraction of provided nanofibrillar materials used to form nanofibrillar architectures could be controlled via immersion in a mixture of ethanol and water. In some embodiments, while deionized water will deswell low concentration silk hydrogels, it was found that ethanol altogether prevented this contraction. In some embodiments, by immersion of nanofibrillar materials in mixtures of water and ethanol, contractions of close to 50% of initial size were induced, dependent on percentage of ethanol in water as shown in FIG. 2 at panel (d). In some embodiments, reducing contraction of nanofibrillar materials leads to lower simulated tensions as shown in FIG. 7, and a lower induced birefringence as shown in FIG. 2 at panel (e).

In some embodiments, nanofibrillar architectures as provided herein are or are capable of large-scale. In some embodiments, provided nanofibrillar architectures span in size on an order of nanoscale to macroscale. In some embodiments, nanofibrillar architectures include nanostructures, microstructures, and/or macrostructures. In some embodiments, nanofibrillar architectures, for example are at least on an order of centimeter scale and larger.

In some embodiments, nanofibrillar architectures are thin structures, having a thickness of less than 100 µm. In some embodiments, nanofibrillar architectures are thick, having a thickness exceeding 200 µm. In some embodiments, nanofibrillar architectures have a thickness in a range of about 500 nm to about 500 µm thick. In some embodiments, nanofibrillar architectures have a thickness of about 500 nm, 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, 500 µm, 550 µm, 600 µm, 750 µm, 1 mm, 2 mm, 3 mm, 4 mm, 5 mm, 10 mm, 100 mm, or thicker.

In some embodiments, nanofibrillar architectures are two dimensional. In some embodiments, nanofibrillar architectures are three dimensional. In some embodiments, the present disclosure provides in-situ generation of both two dimensional and three dimensional, functional multi-component nanofibrillar architecture.

In some embodiments, nanofibrillar architectures are shaped and/or form unique structures. In some embodiments, tension-mediating patterns of anchorages, shapes, and cables were generated through traditional soft lithography. In some embodiments, for example, nanofibrillar architectures having complex microstructures composed of metashapes of triangular, hexagonal (honeycomb), and tri-hexagonal (kagome) cells (~100 um fibers) were generated.

In some embodiments, nanofibrils in provided nanofibrillar architectures are substantially aligned in a direction with increased tension. In some embodiments, high density of nanofibrils correlates with pressed sheet of fibers. In some embodiments, nanofibrils are characterized by higher tension. In some embodiments, nanofibrils are characterized by higher density. In some embodiments, nanofibrils are characterized by lower tension. In some embodiments, nanofibrils are characterized by lower density.

In some embodiments, nanofibrillar architectures exhibit birefringence. In some embodiments, such birefringence corresponds to time and/or stress of compositions or materials when under tension. In some embodiments, birefringence corresponds logarithmically with stress applied in forming nanofibrillar architectures.

In some embodiments, low birefringence ($1^{st}$ order) exhibits relative disorder and minor nanofibril alignment. In some embodiments, increasing birefringence leads first to an emergence of longer fibrils in a span of 15 to 30 degrees from a dominant tension direction. In some embodiments, tension eventually leads to highly aligned fibrils with alignment near exclusively in its dominant tension direction. In some embodiments, high density gels readily formed a thin (typically single layer, <20 nm), porous skin. In some embodiments, birefringence is quantified by a change in refractive index of a nanofibrillar architecture. In some embodiments, ($\eta_1$-$\eta_2$).

Figure 5B:
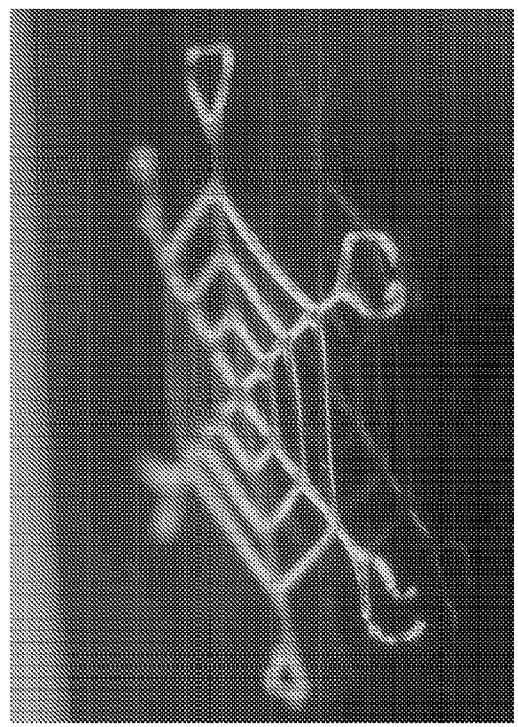
FIG. 5 shows single-shot images of 2 different nanofibrillar webs taken with a camera with macro lens. Sample is placed between crossed polarizers and imaged.
Figure 5A:
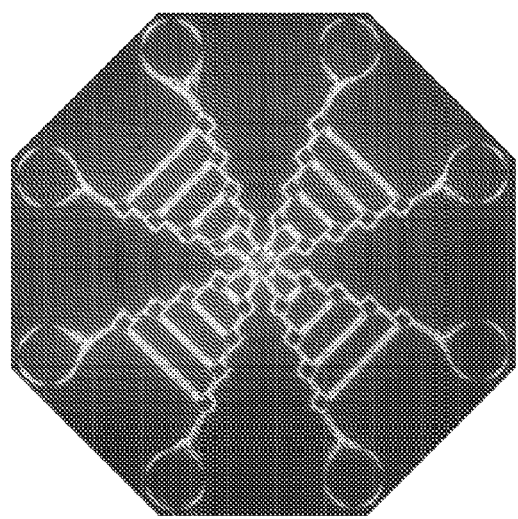
Figure 6:
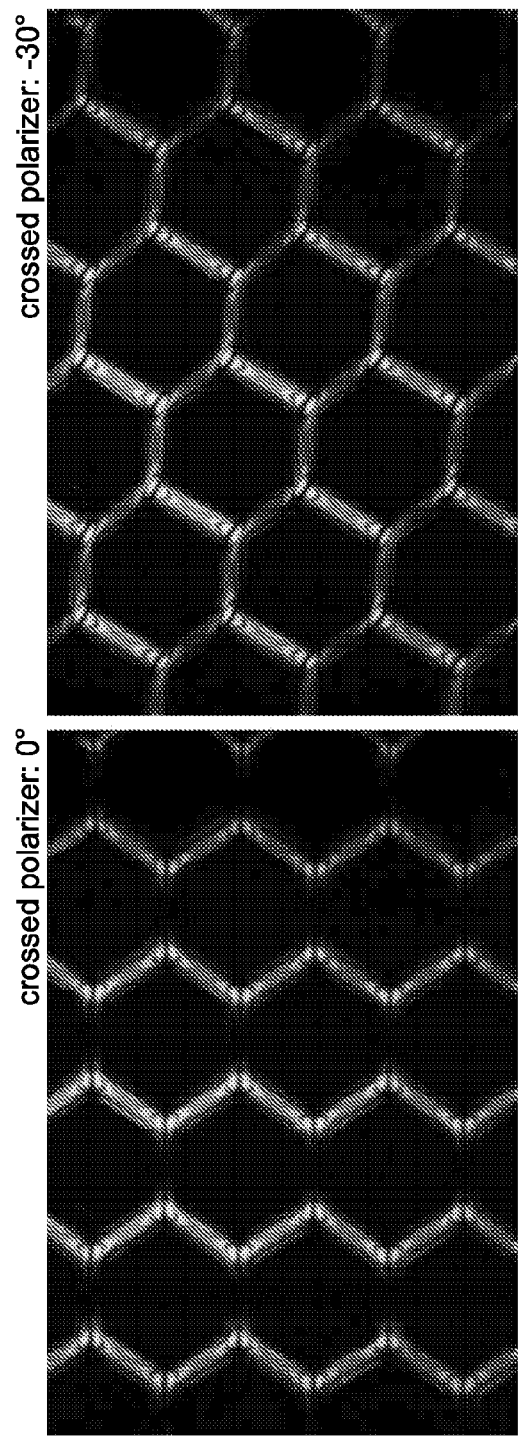
FIG. 6 shows microscope images of a hexagonal (honeycomb) metapattern taken between crossed polarizers oriented at left: 0 degrees, and right: −30 degrees.

In some embodiments, gradients in an alignment of provided nanofibrillar architectures can be verified with polarization microscopy. In some embodiments, through crossed polarizers, provided nanofibrillar architectures display vibrant and controlled gradients of birefringence corresponding to the tensions developed during the induced contraction of the hydrogel as shown in FIG. 5. As shown in FIG. 1 at panel (c), in some embodiments, large nanofibrillar architectures (centimeter scale) composed of trihexagonal and triangular metashapes were assembled, demonstrating multiple length scales at which provided technique operates. In some embodiments, an angle at which polarizers are oriented can reject an appearance that fibers are oriented in a same vector as polarizers, as shown in FIG. 6. In some embodiments, this allows for confirmation of nanofiber directionality in provided nanofibrillar architectures.

In some embodiments, distribution of stresses developed in provided nanofibrillar architectures was modeled using both 2d and 3d Comsol Multiphysics (3d for provided pop-up nanofibrillar architectures), which due to large deformations, were simulated under non-linear conditions as shown in FIG. 2 at panel (a) and FIG. 7. In some embodiments, for example as a test structure, developed stresses in fibers anchored by rings of increasing distance (250 um, 1125 um, and 3125 um) were simulated and contracted by 33% of initial size. Interestingly, in some embodiments, it was found that birefringence contours corresponded logarithmically with stress rather than linearly (this is more apparent with tensed shapes rather than fibers). In some embodiments, increasing ring distance led to higher peak stress, and a higher peak birefringence of provided nanofibrillar architectures.

In some embodiments, for thicknesses of generated nanofibrillar architectures (up to 200 um, at 2 to 5% weight of silk), peak birefringence was found to be in second order green/blue. Strongly aligned fibrils at varying porosity were also evaluated using scanning electron microscopy. In some embodiments, at higher order, a majority of nanofibrils align in a direction of induced tension and at high densities appear akin to a pressed sheet of fibers as shown in FIG. 2 at panel (b). In some embodiments, internal morphology of generated nanofibrillar architectures at various degrees of birefringence was also modeled as shown in FIG. 2 at panel (c). In some embodiments, low birefringence ($1^{st}$ order) exhibit relative disorder and minor nanofibril alignment. In some embodiments, increasing birefringence leads first to an emergence of longer fibrils in a span of 15 to 30° from a dominant direction of tension, eventually leading to highly aligned fibrils aligned substantially in a dominant direction.

Figure 8B:
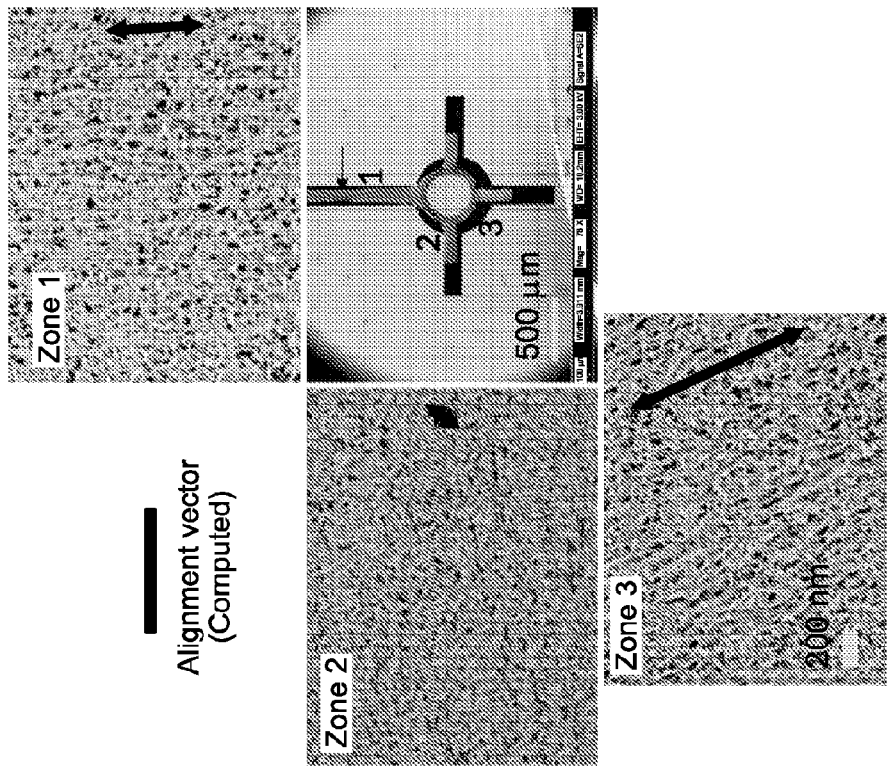
FIG. 8 shows SEM images.
Figure 8A:
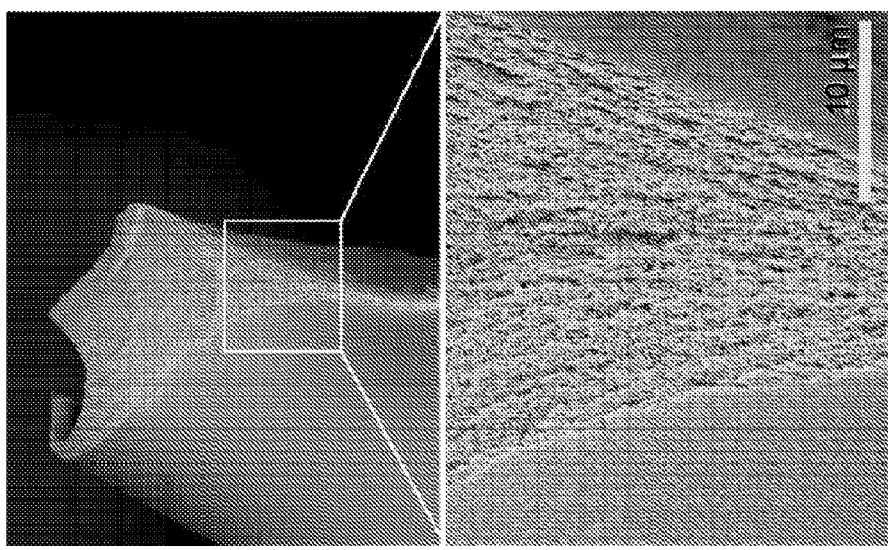

In some embodiments, it was found that high density gels readily formed a thin (typically single layer, <20 nm), porous skin. This is apparent in cleaved nanofibrillar architectures as shown in FIG. 8 at panel (a) whereupon an aligned skin and more porous interior are visible. In addition, a simple test structure with various zones (containing different alignment magnitude and directionality) was generated and verified that such image processing tools (FibrilTool, ImageJ) could determine the directionality and approximate magnitude of nanofiber morphology as shown in FIG. 8 at panel (b).

Figure 10:
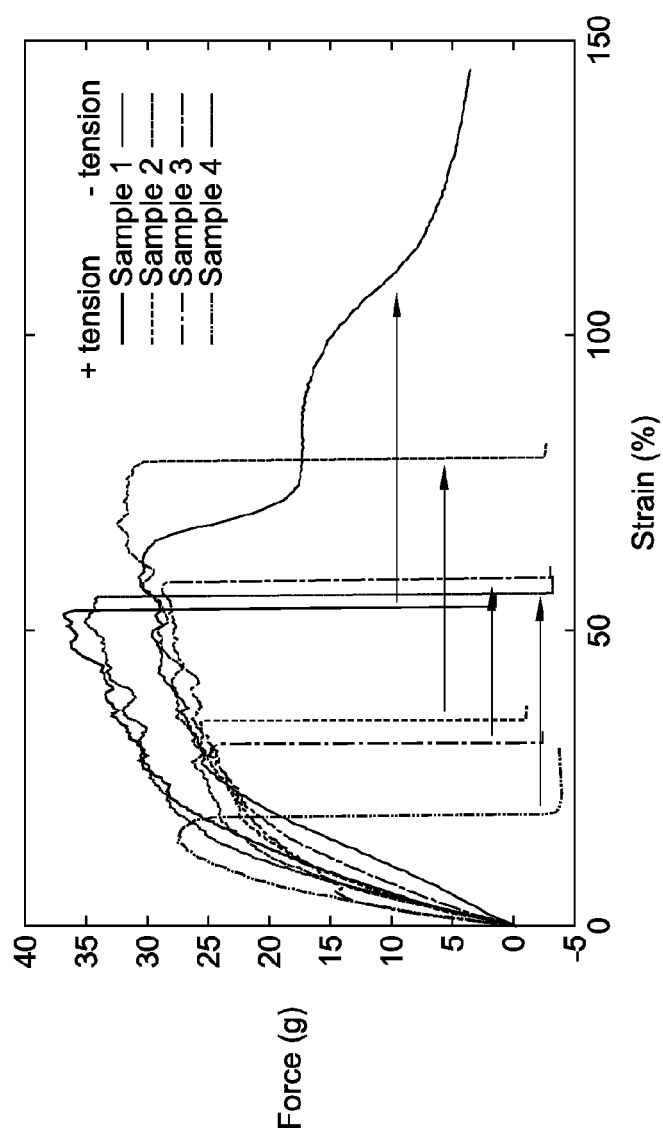
FIG. 10 shows force strain curves for fibers under tensile stress. Strained fibers display a high initial strength (FIG. 2), however display lower plasticity and strain to break.
Figure 11:
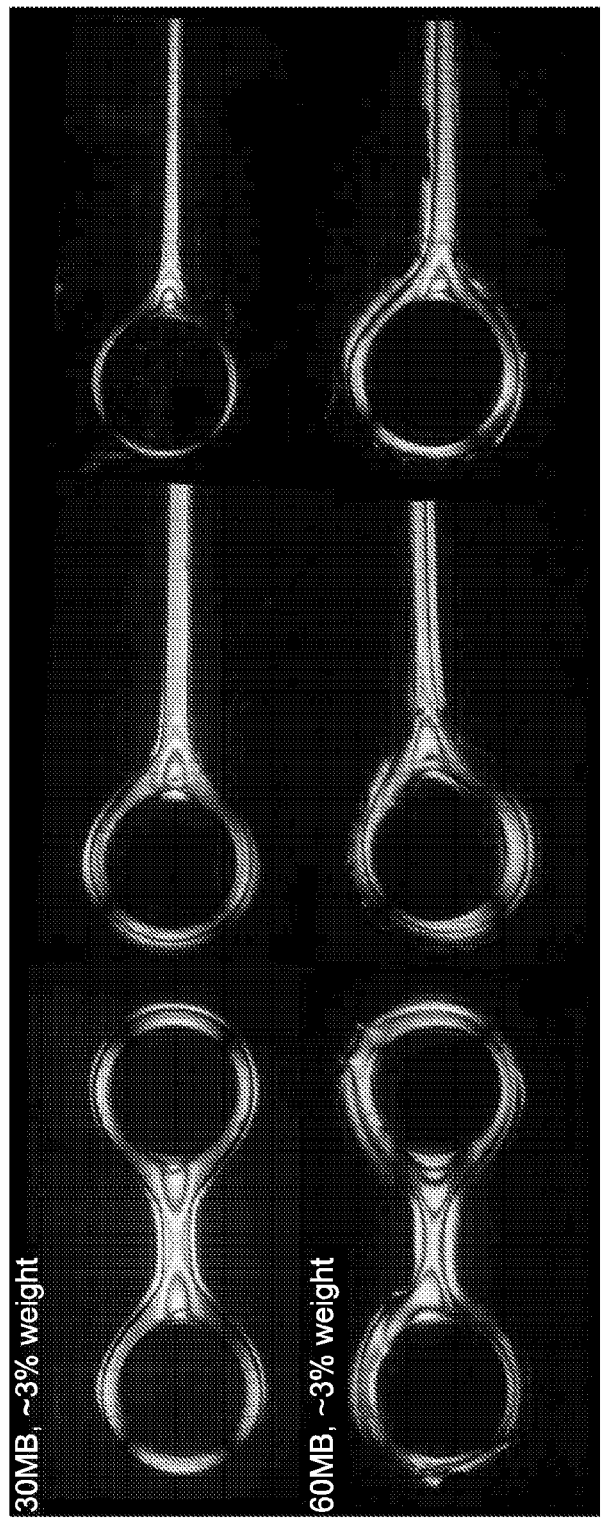
FIG. 11 shows birefringence of samples generated from 30 minute-boil and 60 minute-boil silk at approximately 50% contraction. Reduction of silk fibroin molecular weight generally leads to a weaker hydrogel, and it was found that this led to a reduced birefringence and a more inconsistent final structure.

In some embodiments, dynamic mechanical analysis was utilized to determine an effect of nanofibril organization on mechanical properties of certain provided nanofibrillar architectures. In some embodiments, test nanofibrillar architectures possessing fibers of both low and high alignment within a same structure (this was generating by designing a mold anchor for one fiber in the test structure by not the other) were generated. In some embodiments, this lead to nanofibrillar architectures of equivalent density and contraction, yet possessing differing nanofibrillar alignment (and birefringence) due to tension induced by the presence or lack thereof of an anchorage as shown in FIG. 2 at panel (f). In some embodiments, it was found that untensed and tensed fibers possessed differing mechanical properties. In some embodiments, tensed fibers possessed an increased low-strain elasticity as shown in FIG. 2 at panel (g), a consequence of a physical transformation of a structure and possibly of a strain-stiffening response that occurs at times with silk hydrogel. In some embodiments, untensed fibers, however, possessed higher plasticity and a larger strain to break as shown in FIG. 10 due to residual mechanical structure disorder.

In some embodiments, effects of mechanical constraints on nano- and micro-scale morphology of certain provided nanofibrillar particles were investigated. In some embodiments, cylindrical particles constrained by simple 2× and 4× spaced anchorages transform these shapes; 2 anchorages increase an eccentricity of a cylindrical shape, while 4 anchorages alters this cylinder into a concave square as shown in FIG. 3 at panel (a). In some embodiments, these transformations were accompanied by an emergence of birefringent patterns corresponding to tensions developed during formation of these new shapes. In some embodiments, it was found that such tensions on particles drove both heterogeneity in apparent nanofibril density and orientation across such nanofibrillar architectures as shown in FIG. 3 at panel (b). In some embodiments, as a test structure, an elliptic cylinder (formed from 1.0% silk, exact shape shown in outline of the Comsol simulations, as shown in FIG. 3 at panel (c)) with varying degrees of eccentricity at four distal points of the shape was constrained. In some embodiments, surface morphology of high eccentricity, high contraction elliptic cylinders was assayed under SEM. In some embodiments, nanofibrils orient along directions of stress and increase in density and alignment across nanofibrillar architectures with increasing stress/strain. In some embodiments, these transformations suggest nonlinearities in a response of certain provided porous material to strain, as high compressive forces increase the apparent density of the structure. In some embodiments, response using fluorescent-particle doped nanofibrillar architectures was attempted. In some embodiments, as shown in FIG. 3 at panel (c), top-down fluorescence of such nanofibrillar architectures polarize in accordance with birefringence and stress. An origin of this effect was verified using confocal microscopy as shown in FIG. 12. Without wishing to be held to a particular theory, in some embodiments, it appears a cause of polarity may come from a combination of two effects: 1) an increased thickness at regions of high stress, and 2) higher concentration of fluorescent nanoparticles (presumably accompanying a higher density structure) at these regions.

Figure 4E:
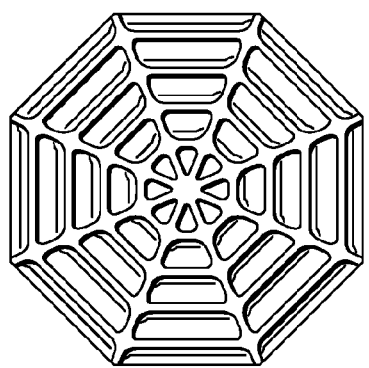
FIG. 4 shows a functional nanofibrillar architecture.
Figure 4G:
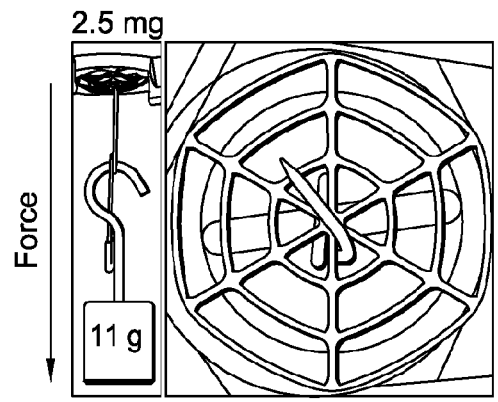
Figure 4F:
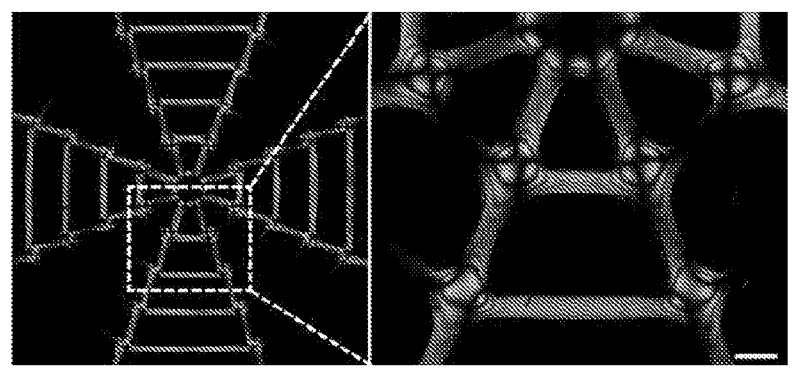
Figures 13A, 13B:
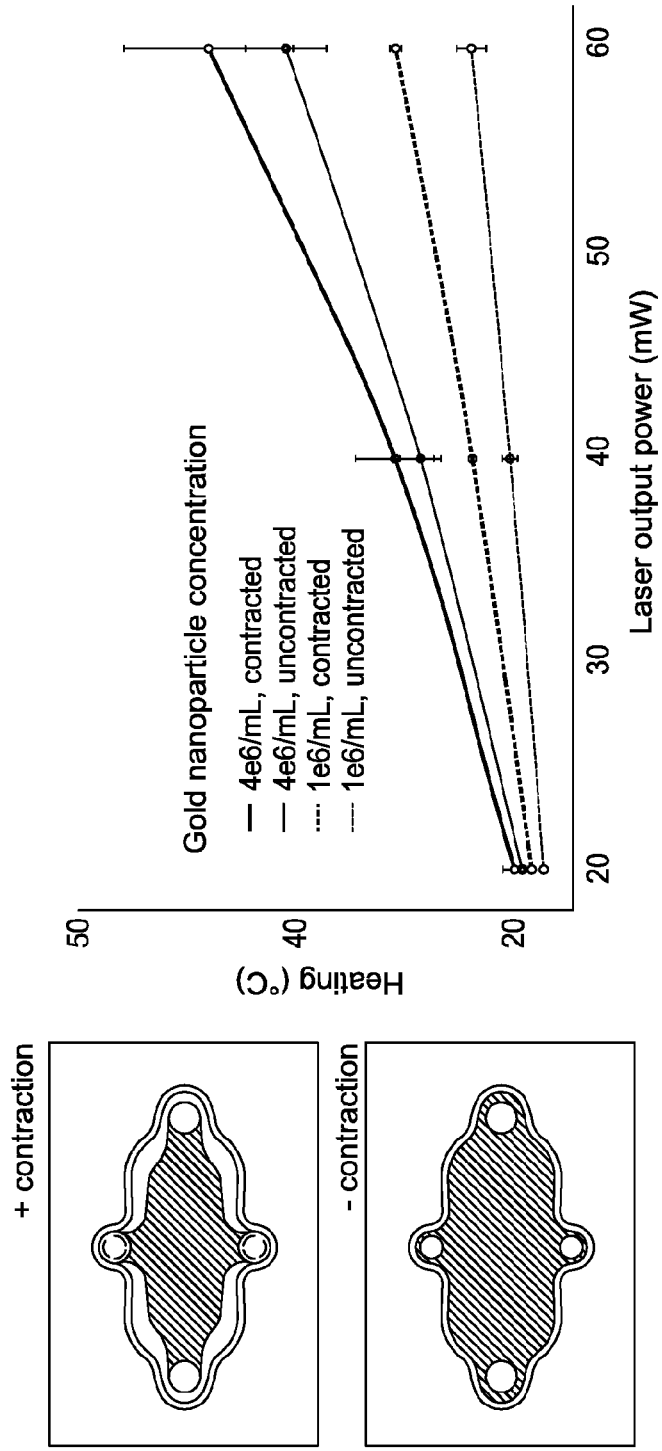
FIG. 13 shows gold doped materials.
Figure 14B:
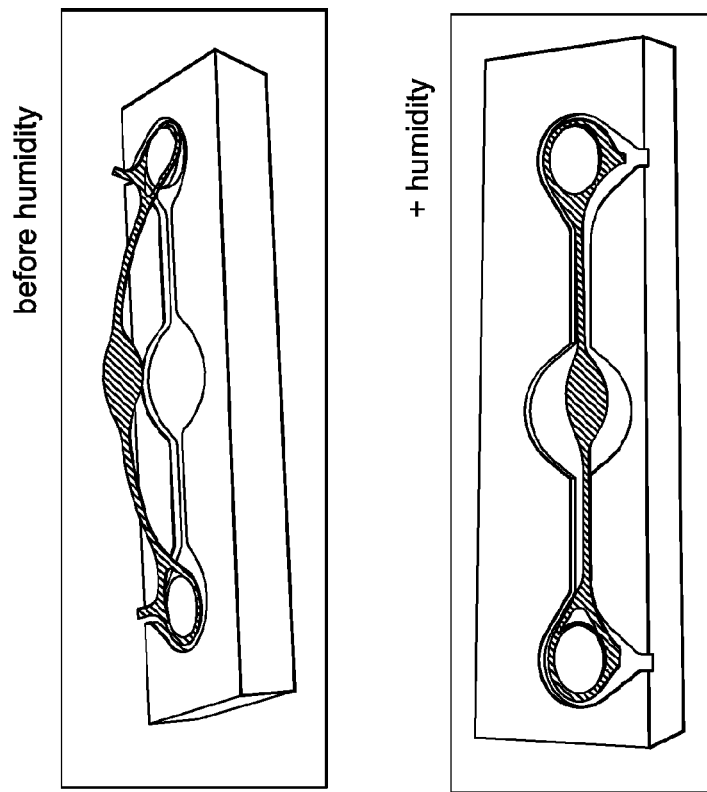
FIG. 14 shows molding.
Figure 14A:
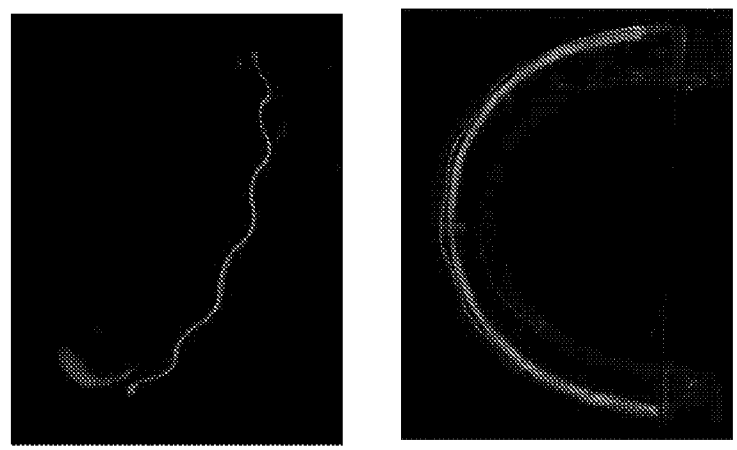
Figure 15:
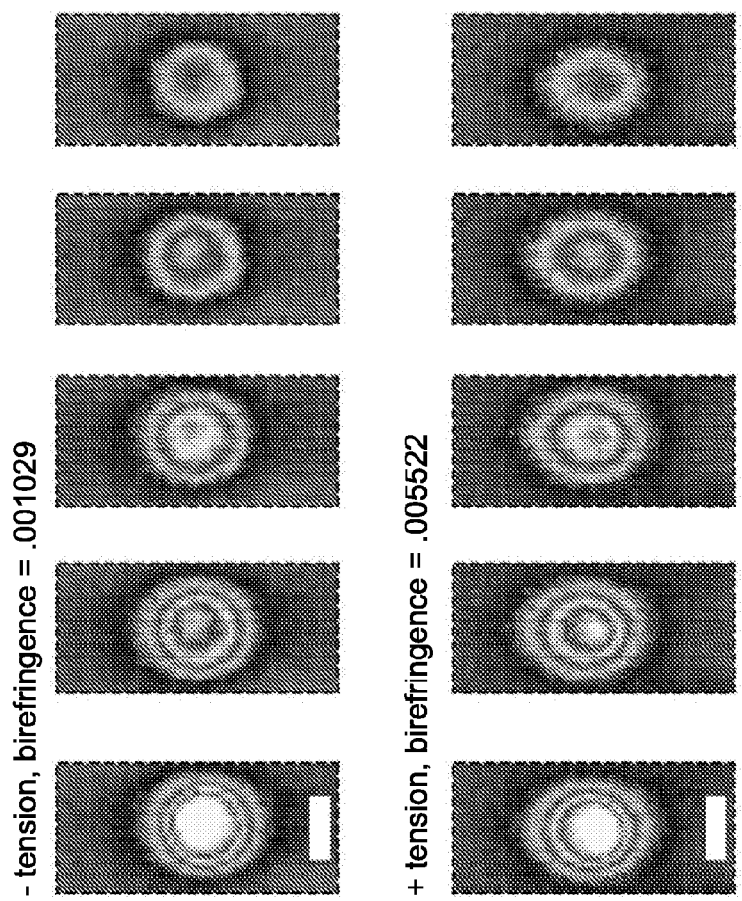
FIG. 15 shows infrared thermography of provided gold nanoparticle doped-native nanofibrillar combination test structures with equivalent widths (~2 cm). Higher alignment leads to eccentric thermal dissipation irrespective of test structure width.

The ability of provided techniques, in some embodiments, to create architectural structure was studied. In this vein, creating 3-dimensional nanofibrillar shapes was a first of studied techniques. In some embodiments viable approaches for forming three dimensional nanofibrillar architectures include, for example, as shown in FIG. 3 at panel (d): 1) induction of buckling instabilities by engineered anchor-points, 2) buckling of long, aligned fibers due to aligned nanofibril swelling at ambient humidity, and 3) direct deformation of the PDMS mold as shown in FIG. 13 at panel (b). In some embodiments, simple 2-anchor buckling instabilities were generated by placing these at an edge of thin plates or oriented around a corner. In some embodiments, three-dimensional simulations (nonlinear mechanical modelling in Comsol Multiphysics) illustrate high stress regions and positions of induced z-displacement. In some embodiments, contraction restricts z-motion at locations of high tensile stress (connecting from anchorage to anchorage), however generates large compressive stress perpendicular to these contours, inducing z-dimensional buckling of provided nanofibrillar architectures as shown in FIG. 3 at panel (f). 3-dimensional shape of corner-oriented anchorages with increasing contraction is shown in FIG. 4 at panel (d). In some embodiments, low contractions yield a deflection at the pointed tip of the structure (as shown in simulations), moderate contractions pop this structure so as to point in the z-direction, whereas large contractions induces complete curling of the structure 180 degrees from initial orientation. In some embodiments, generation of tensile stress at the edges of thin plates leads to z-motion in unanchored regions, forming cup or flower-like morphologies as shown in FIG. 4 at panel (e). In some embodiments, buckling instabilities could be generated directly via swelling of long aligned fibril beams.

Examples of these nanofibrillar architectures and corresponding fiber birefringence are shown in FIG. 4 at panel (f). In some embodiments, higher contractions and larger nanofibril alignment led to large buckling displacements. In some embodiments, swelling-induced buckling was only noticed on fibers of an aspect ratio of greater 15:1. This effect was achieved with consistency. In some embodiments, buckling however was highly sensitive to a number of fabrication parameters including critical-point-time, ethanol dehydration time among others. It was surmised that in some embodiments, these parameters affect hygroscopic and swelling properties of silk nanofibrils.

In some embodiments, an environmental-responsive nature of these nanofibrillar architectures was tested by exposing them to 75% and 95% humidity in a humidified chamber as shown in FIG. 4 at panel (g) and FIG. 4 at panel (h). In some embodiments, water acts as a softener/plasticizer for silk fibroin (reducing its strength while significantly improving its flexibility), and exposure to high humidity caused provided nanofibrillar architectures to collapse under their own weight at a rate dependent on surrounding vapor. In some embodiments, immediately and long after exposure to humidity, provided nanofibrillar architectures retained a light blue scattering appearance of an aerogel, however, did not rebuckle in its z-direction to their initial pop-up shape as shown in FIG. 13 at panel (c). It is believed that provided nanofibril nanofibrillar architectures undergo multiple transformations with introduction of water, beginning with anisotropic swelling (40 to 50%), before becoming permanently softened (70-90%) with increased infiltration of moisture at exposure to higher humidity.

In some embodiments, laser-heating and corresponding infrared thermography of such nanofibrillar architectures revealed an asymmetry in the thermal transport of tensed versus untensed nanofibrillar architectures as shown in FIG. 3 at panel (f), consistent with other studies on infrared thermography on aligned fibers[37]. In some embodiments, aligned nanofibrillar architectures display both an eccentric thermal signature, and in addition a unique sharp tail at the edges of this signature in the direction of structure alignment. In some embodiments, thermal-signature-eccentricity was plotted over time and as a function of the structure birefringence/alignment. In some embodiments, more aligned nanofibrillar architectures displayed higher eccentricities that increased over time as the heat dissipated in the structure. In some embodiments, induction of different birefringence/alignment of nanofibrillar architectures required contraction at different percentages, and which corresponded to changes to the structure width. In some embodiments, aligned and unaligned nanofibrillar architectures were generated with equivalent width (+/−5%) contracting from higher width molds. Unfortunately, due to reduced tensions developed in these nanofibrillar architectures, it was difficult to obtain an equivalent alignment to that which was achieved in lower width nanofibrillar architectures (these nanofibrillar architectures were also bent in a curve to increase mechanical tension), however infrared thermography nevertheless revealed the increased eccentricity of the thermal signature of comparable width aligned vs. unaligned nanofibrillar architectures (example shown in FIG. 12).

In some embodiments, full, nanofibrillar architectural webs (approximately 2 cm diameter, from 5% weight silk fibroin hydrogel) were generated demonstrating both scale and mechanical functionality. In some embodiments, control of in generating nano to macro-scale order is evidenced by structural birefringence as shown in FIG. 4 at panel (i). Web draglines exhibit gradients in alignment in accordance with tensions developed on nanofibrillar architectures during contraction that are consistent across nanofibrillar architectures in their entirety. Web centers were loaded with point loads to examine their mechanical performance. Deflection of one such web (~2.5 mg mass) under a 0.11 N point load (11 g) is shown in FIG. 4 at panel (j). These webs generally sustain masses close to 20 g, before failure at the dragline junction points. Without wishing to be held to a particular theory, this is likely due to the combination of large stresses focused at these junctions while these points are also weaker due to reduced alignment in comparison to the dragline fibers. It was surmised that these failure points could be alleviated through an optimized mechanical design.

The present disclosure provides herein a new approach of engineering properties of nanofibrillar structure at multiple size scales (at nano-, micro-, and macro-sizes). In some embodiments, provided methods are based, in part, on initial generation of a patterned, intermediate hydrogel upon which tensions are introduced via substrate deformation or hydrogel contraction. Tensed/biased nanofibrillar architectures may then be re-entrapped in this state via a secondary crystallization step.

In some embodiments, mechanical tension mediated through anchorages and cables yield permanent transitions in structure nano-morphology and x, y, and z-dimensional size. While certain provided examples included silk for a recrystallization step, it is believed that this approach could be adapted directly to other biomaterials (such as cellulose via its own secondary crystallization), or in standard hydrogels via secondary chemical linkages or structural encasement (and eventually adapted to shaping structure in 3d-shaped hydrogel). In addition, in some embodiments, such engineered primary nanofibrillar architectures could become a template for generating secondary nanofibrillar architectures, whether via polymerization of material on existing fibrils or direct pyrolysis of such nanofibrillar architectures, enabling a suite of potential supplementary applications.

Nanofibrillar Biopolymers
Silk

In some embodiments, a polypeptide is or comprises a silk polypeptide, such as a silk fibroin polypeptide. In nature, silk is produced as protein fiber, typically made by specialized glands of animals, and often used in nest construction. Organisms that produce silk include the Hymenoptera (bees, wasps, and ants and other types of arthropods, most notably various arachnids such as spiders (e.g., spider silk), also produce silk. Silk fibers generated by insects and spiders represent the strongest natural fibers known and rival even synthetic high performance fibers.

The first reported examples of silk being used as a textile date to ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, N.J. (2004)); it has been highly prized in that industry ever since. Indeed, silk has been extensively investigated for its potential in textile, biomedical, photonic and electronic applications. Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)). Thus, even among biocompatible polymers (and particularly among biocompatible polypeptides, including natural polypeptides), silk and silk polypeptides are of particular interest and utility.

Silk fibroin is a polypeptide, like collagen, but with a unique feature: it is produced from the extrusion of an amino-acidic solution by a living complex organism (while collagen is produced in the extracellular space by self-assembly of cell-produced monomers). Silk is naturally produced by various species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis*. Embodiments of the present disclosure may utilize silk proteins from any such organism. In some embodiments, the present disclosure utilizes silk or silk proteins from a silkworm, such as *Bombyx mori* (e.g., from cocoons or glands thereof). In some embodiments, the present disclosure utilizes silks or silk proteins from a spider, such as *Nephila clavipes* (e.g., from nests/webs or glands thereof).

In general, silk polypeptides for use in accordance with the present disclosure may be or include natural silk polypeptides, or fragments or variants thereof. In some embodiments, such silk polypeptides may be utilized as natural silk, or may be prepared from natural silk or from organisms that produce it. Alternatively, silk polypeptides utilized in the present disclosure may be prepared through an artificial process, for example, involving genetic engineering of cells or organisms (e.g., genetically engineered bacteria, yeast, mammalian cells, non-human organisms, including animals, or transgenic plants) to produce a silk polypeptide, and/or by chemical synthesis.

In some particular embodiments, silk polypeptides are obtained from cocoons produced by a silkworm, in certain embodiments by the silkworm Bombyx mori; such cocoons are of particular interest as a source of silk polypeptide because they offer low-cost, bulk-scale production of silk polypeptides. Moreover, isolation methodologies have been developed that permit preparation of cocoon silk, and particularly of Bombyx mori cocoon silk in a variety of forms suitable for various commercial applications.

Silkworm cocoon silk contains two structural proteins, the fibroin heavy chain (~350 kDa) and the fibroin light chain (~25 kDa), which are associated with a family of non-structural proteins termed sericins, that glue the fibroin chains together in forming the cocoon. The heavy and light fibroin chains are linked by a disulfide bond at the C-terminus of the two subunits (see Takei, et al. J. Cell Biol., 105: 175, 1987; see also Tanaka, et al J. Biochem. 114: 1, 1993; Tanaka, et al Biochim. Biophys. Acta., 1432: 92, 1999; Kikuchi, et al Gene, 110: 151, 1992). The sericins are a high molecular weight, soluble glycoprotein constituent of silk which gives the stickiness to the material. These glycoproteins are hydrophilic and can be easily removed from cocoons by boiling in water. This process is often referred to as "degumming." In some embodiments, silk polypeptide compositions utilized in accordance with the present disclosure are substantially free of sericins (e.g., contain no detectable sericin or contain sericin at a level that one of ordinary skill in the pertinent art will consider negligible for a particular use).

To give but one particular example, in some embodiments, silk polypeptide compositions for use in accordance with the present disclosure are prepared by processing cocoons spun by silkworm, *Bombyx mori* so that sericins are removed and silk polypeptides are solubilized. In some such embodiments, cocoons are boiled (e.g., for a specified length of time, often approximately 30 minutes) in an aqueous solution (e.g., of 0.02 M $Na_2CO_3$), then rinsed thoroughly with water to extract the glue-like sericin proteins. Extracted silk is then dissolved in a solvent, for example, LiBr (such as 9.3 M). A resulting silk fibroin solution can then be further processed for a variety of applications as described elsewhere herein.

In some embodiments, silk polypeptide compositions for use in the practice of the present disclosure comprise silk fibroin heavy chain polypeptides and/or silk fibroin light chain polypeptides; in some such embodiments, such compositions are substantially free of any other polypeptide. In some embodiments that utilize both a silk fibroin heavy chain polypeptide and a silk fibroin light chain polypeptide, the heavy and light chain polypeptides are linked to one another via at least one disulfide bond. In some embodiments, where the silk fibroin heavy and light chain polypeptides are present, they are linked via one, two, three or more disulfide bonds.

Exemplary natural silk polypeptides that may be useful in accordance with the present disclosure may be found in International Patent Publication Number WO 2011/130335, International Patent Publication Number WO 97/08315 and/or U.S. Pat. No. 5,245,012, the entire contents of each of which are incorporated herein by reference. Table 1, below, provides an exemplary list of silk-producing species and silk proteins:

TABLE 1

An exemplary list of silk-producing species and silk proteins
(adopted from Bini et al. (2003), J. Mol. Biol. 335(1): 27-40).

| Accession | Species | Producing gland | Protein |
|---|---|---|---|
| Silkworms | | | |
| AAN28165 | *Antheraea mylitta* | Salivary | Fibroin |
| AAC32606 | *Antheraea pernyi* | Salivary | Fibroin |
| AAK83145 | *Antheraea yamamai* | Salivary | Fibroin |
| AAG10393 | *Galleria mellonella* | Salivary | Heavy-chain fibroin (N-terminal) |
| AAG10394 | *Galleria mellonella* | Salivary | Heavy-chain fibroin (C-terminal) |
| P05790 | *Bombyx mori* | Salivary | Fibroin heavy chain precursor, Fib-H, H-fibroin |
| CAA27612 | *Bombyx mandarina* | Salivary | Fibroin |
| Q26427 | *Galleria mellonella* | Salivary | Fibroin light chain precursor, Fib-L, L-fibroin, PG-1 |
| P21828 | *Bombyx mori* | Salivary | Fibroin light chain precursor, Fib-L, L-fibroin |
| Spiders | | | |
| P19837 | *Nephila clavipes* | Major ampullate | Spidroin 1, dragline silk fibroin 1 |
| P46804 | *Nephila clavipes* | Major ampullate | Spidroin 2, dragline silk fibroin 2 |
| AAK30609 | *Nephila senegalensis* | Major ampullate | Spidroin 2 |
| AAK30601 | *Gasteracantha mammosa* | Major ampullate | Spidroin 2 |
| AAK30592 | *Argiope aurantia* | Major ampullate | Spidroin 2 |
| AAC47011 | *Araneus diadematus* | Major ampullate | Fibroin-4, ADF-4 |
| AAK30604 | *Latrodectus geometricus* | Major ampullate | Spidroin 2 |
| AAC04503 | *Araneus bicentenarius* | Major ampullate | Spidroin 2 |
| AAK30615 | *Tetragnatha versicolor* | Major ampullate | Spidroin 1 |
| AAN85280 | *Araneus ventricosus* | Major ampullate | Dragline silk protein-1 |
| AAN85281 | *Araneus ventricosus* | Major ampullate | Dragline silk protein-2 |
| AAC14589 | *Nephila clavipes* | Minor ampullate | MiSp1 silk protein |
| AAK30598 | *Dolomedes tenebrosus* | Ampullate | Fibroin 1 |
| AAK30599 | *Dolomedes tenebrosus* | Ampullate | Fibroin 2 |
| AAK30600 | *Euagrus chisoseus* | Combined | Fibroin 1 |
| AAK30610 | *Plectreurys tristis* | Larger ampule-shaped | Fibroin 1 |
| AAK30611 | *Plectreurys tristis* | Larger ampule-shaped | Fibroin 2 |
| AAK30612 | *Plectreurys tristis* | Larger ampule-shaped | Fibroin 3 |
| AAK30613 | *Plectreurys tristis* | Larger ampule-shaped | Fibroin 4 |
| AAK30593 | *Argiope trifasciata* | Flagelliform | Silk protein |
| AAF36091 | *Nephila madagascariensis* | Flagelliform | Fibroin, silk protein (N-terminal) |
| AAF36092 | *Nephila madagascariensis* | Flagelliform | Silk protein (C-terminal) |
| AAC38846 | *Nephila clavipes* | Flagelliform | Fibroin, silk protein (N-terminal) |
| AAC38847 | *Nephila clavipes* | Flagelliform | Silk protein (C-terminal) |

Silk fibroin polypeptides are characterized by a structure that typically reflects a modular arrangement of large hydrophobic blocks staggered by hydrophilic, acidic spacers, and, typically, flanked by shorter (~100 amino acid), often highly conserved, terminal domains (at one or both of the N and C termini). In many embodiments, the hydrophobic blocks comprise or consist of alanine and/or glycine residues; in some embodiments alternating glycine and alanine; in some embodiments alanine alone. In many embodiments, the hydrophilic spacers comprise or consist of amino acids with bulky side-groups. Naturally occurring silk fibroin polypeptides often have high molecular weight (200 to 350 kDa or higher) with transcripts of 10,000 base pairs and higher and >3000 amino acids (reviewed in Omenetto and Kaplan (2010) Science 329: 528-531).

In some embodiments, core repeat sequences of the hydrophobic blocks found in silk fibroin polypeptides are represented by one or more of the following amino acid sequences and/or formulae:

```
                                          (SEQ ID NO: 1)
(GAGAGS)5-15;

(SEQ ID NO: 2)
(GX)5-15 (X = V, I, A);

(SEQ ID NO: 3)
GAAS;

(SEQ ID NO: 4)
(S1-2A11-13);

(SEQ ID NO: 5)
GX1-4 GGX;

(SEQ ID NO: 6)
GGGX (X = A, S, Y, R, D V, W, R, D);

(SEQ ID NO: 7)
(S1-2A1-4)1-2;

(SEQ ID NO: 8)
GLGGLG;

(SEQ ID NO: 9)
GXGGXG (X = L, I, V, P);

(SEQ ID NO: 10)
GPX (X = L, Y, I); (GP(GGX)1-4 Y)n (X = Y, V, S, A);

(SEQ ID NO: 11)
GRGGAn;

(SEQ ID NO: 12)
GGXn (X = A, T, V, S); GAG(A)6-7GGA;
and (SEQ ID NO: 13)
GGX GX GXX (X = Q, Y, L, A, S, R).
```

In some embodiments, a fibroin polypeptide contains multiple hydrophobic blocks, e.g., 3, 4, 5, 6, 7, 8, 9, 10, 11, 12, 13, 14, 15, 16, 17, 18, 19 and 20 hydrophobic blocks within the polypeptide. In some embodiments, a fibroin polypeptide contains between 4-17 hydrophobic blocks. In some embodiments, a fibroin polypeptide comprises at least one hydrophilic spacer sequence ("hydrophilic block") that is about 4-50 amino acids in length. Non-limiting examples of such hydrophilic spacer sequences include:

TGSSGFGPYVNGGYSG; (SEQ ID NO: 14)

YEYAWSSE; (SEQ ID NO: 15)

SDFGTGS; (SEQ ID NO: 16)

RRAGYDR; (SEQ ID NO: 17)

EVIVIDDR; (SEQ ID NO: 18)

TTIIEDLDITIDGADGPI (SEQ ID NO: 19)
and

TISEELTI. (SEQ ID NO: 20)

In certain embodiments, a fibroin polypeptide contains a hydrophilic spacer sequence that is a variant of any one of the representative spacer sequences listed above. In some embodiments, a variant spacer sequence shows at least 75%, at least 80%, at least 85%, at least 90%, or at least 95% identity to one or more of the hydrophilic spacer sequences listed above, which may be considered to be reference hydrophilic spacer sequences.

In some embodiments, a fibroin polypeptide suitable for the present disclosure does not contain any of the hydrophilic spacer sequences listed above; in some embodiments, such a fibroin polypeptide further does not contain any variant of such a hydrophilic spacer sequence.

It is generally believed that features of silk fibroin polypeptide structure contribute to the material properties and/or functional attributes of the polypeptide. For example, sequence motifs such as poly-alanine (polyA) and polyalanine-glycine (poly-AG) are inclined to be beta-sheet-forming; the presence of one or more hydrophobic blocks as described herein therefore may contribute to a silk polypeptide's ability to adopt a beta-sheet conformation, and/or the conditions under which such beta-sheet adoption occurs.

In some embodiments, the silk fiber can be an unprocessed silk fiber, e.g., raw silk or raw silk fiber. The term "raw silk" or "raw silk fiber" refers to silk fiber that has not been treated to remove sericin, and thus encompasses, for example, silk fibers taken directly from a cocoon. Thus, by unprocessed silk fiber is meant silk fibroin, obtained directly from the silk gland. When silk fibroin, obtained directly from the silk gland, is allowed to dry, the structure is referred to as silk I in the solid state. Thus, an unprocessed silk fiber comprises silk fibroin mostly in the silk I conformation (a helix dominated structure). A regenerated or processed silk fiber on the other hand comprises silk fibroin having a substantial silk II (a β-sheet dominated structure).

Inducing a conformational change in silk fibroin can facilitate formation of a solid-state silk fibroin and/or make the silk fibroin at least partially insoluble. Further, inducing formation of beta-sheet conformation structure in silk fibroin can prevent silk fibroin from contracting into a compact structure and/or forming an entanglement. In some embodiments, a conformational change in the silk fibroin can alter the crystallinity of the silk fibroin in the silk particles, such as increasing crystallinity of the silk fibroin, e.g., silk II beta-sheet crystallinity. In some embodiments, the conformation of the silk fibroin in the silk fibroin foam can be altered after formation.

In some embodiments, bio-ink compositions as disclosed herein cure to possess some degree of silk II beta-sheet crystallinity.

In some embodiments, bio-ink compositions that cure form printed articles with a high degree of silk II beta-sheet crystallinity. In some embodiments, bio-ink compositions that subsequently form printed articles with a high degree of silk II beta-sheet crystallinity are insoluble to solvents. In some embodiments, bio-ink compositions that subsequently form printed articles with a high degree of silk II beta-sheet crystallinity are insoluble to immersion in solvents. In some embodiments, bio-ink compositions that subsequently form printed articles with a high degree of silk II beta-sheet crystallinity are insoluble when layers of a bio-ink composition are subsequently printed, deposited, and/or extruded atop a printed article.

In some embodiments, bio-ink compositions that cure form printed articles with a low degree of silk II beta-sheet crystallinity. In some embodiments, bio-ink compositions that subsequently form printed articles with a low degree of silk II beta-sheet crystallinity are at least partially soluble to solvents. In some embodiments, bio-ink compositions that subsequently form printed articles with a low degree of silk II beta-sheet crystallinity are at least partially soluble when layers of a bio-ink composition are subsequently printed, deposited, and/or extruded atop a printed article.

In some embodiments, physical properties of silk fibroin can be modulated when selecting and/or altering a degree of crystallinity of silk fibroin. In some physical properties of silk fibroin include, for example, mechanical strength, degradability, and/or solubility. In some embodiments, inducing a conformational change in silk fibroin can alter the rate of release of an active agent from the silk matrix.

In some embodiments, a conformational change can be induced by any methods known in the art, including, but not limited to, alcohol immersion (e.g., ethanol, methanol), water annealing, water vapor annealing, heat annealing, shear stress (e.g., by vortexing), ultrasound (e.g., by sonication), pH reduction (e.g., pH titration), and/or exposing the silk particles to an electric field and any combinations thereof.

Also, GXX motifs contribute to 31-helix formation; GXG motifs provide stiffness; and, GPGXX (SEQ ID NO: 22) contributes to beta-spiral formation. In light of these teachings and knowledge in the art (see, for example, review provided by Omenetto and Kaplan Science 329: 528, 2010), those of ordinary skill, reading the present specification, will appreciate the scope of silk fibroin polypeptides and variants thereof that may be useful in practice of particular embodiments of the present disclosure.

In some embodiments, bio-ink compositions as disclosed herein are or comprise a silk ionomeric composition. In some embodiments, bio-ink compositions as disclosed herein are or comprise ionomeric particles distributed in a solution. (See for example, WO 2011/109691 A2, to Kaplan et al., entitled Silk-Based Ionomeric Compositions, which describes silk-based ionomeric compositions and methods of manufacturing, which is hereby incorporated by reference in its entirety herein).

In some embodiments, bio-ink compositions comprising silk-based ionomeric particles may exist in fluid suspensions (or particulate solutions) or colloids, depending on the concentration of the silk fibroin. In some embodiments, bio-ink compositions comprising ionmeric particles include positively and negatively charged silk fibroin associated via electrostatic interaction.

In some embodiments, silk ionomeric particles are reversibly cross-linked through electrostatic interactions. In some embodiments, silk ionomeric compositions reversibly transform from one state to the other state when exposed to an environmental stimulus. In some embodiments, environmental stimuli silk ionomeric compositions respond to include for example, a change in pH, a change in ionic strength, a change in temperature, a change in an electrical current applied to the composition, or a change on a mechanical stress as applied to the composition. In some embodiments, silk ionomeric compositions transform into a dissociated charged silk fibroin solution.

Keratins

Keratins are members of a large family of fibrous structural proteins (see, for example, Moll et al, Cell 31:11 1982 that, for example, are found in the outer layer of human skin, and also provide a key structural component to hair and nails. Keratin monomers assemble into bundles to form intermediate filaments, which are tough and insoluble and form strong unmineralized tissues found in reptiles, birds, amphibians, and mammals.

Two distinct families of keratins, type I and type II, have been defined based on homologies to two different cloned human epidermal keratins (see Fuchs et al., Cell 17:573, 1979, which is hereby incorporated by reference in its entirety herein). Like other intermediate filament proteins, keratins contain a core structural domain (typically approximately 300 amino acids long) comprised of four segments in alpha-helical conformation separated by three relatively short linker segments predicted to be in beta-turn confirmation (see Hanukoglu & Fuchs Cell 33:915, 1983, which is hereby incorporated by reference in its entirety herein). Keratin monomers supercoil into a very stable, left-handed superhelical structure; in this form, keratin can multimerise into filaments. Keratin polypeptides typically contain several cysteine residues that can become crosslinked In some embodiments, bio-ink compositions for use in the practice of the present disclosure comprise one or more keratin polypeptides.

Biopolymer Properties

Molecular Weight

The present disclosure appreciates that preparations of a particular biopolymer that differ in the molecular weight of the included biopolymer (e.g., average molecular weight and/or distribution of molecular weights) may show different properties relevant to practice of the present disclosure, including, for example, different viscosities and/or flow characteristics, different abilities to cure, etc. In some embodiments, a molecular weight of a biopolymer may impact a self-life of a bio-ink composition. Those of ordinary skill, reading the present disclosure and armed with knowledge in the art, will be able to prepare and utilize various bio-ink compositions with appropriate molecular weight characteristics for relevant embodiments of the invention.

In some particular embodiments, bio-ink compositions for use in accordance with the present disclosure include biopolymers whose molecular weight is within a range bounded by a lower limit and an upper limit, inclusive. In some embodiments, the lower limit is at least 1 kDa, at least 5 kDa, at least 10 kDa, at least 15 kDa, at least 20 kDa, at least 25 kDa, at least 30 kDa, at least 40 kDa, at least 50 kDa, at least 60 kDa, at least 70 kDa, at least 80 kDa, at least 90 kDa, at least 100 kDa, at least 150 kDa, at least 200 kDa; in some embodiments, the upper limit is less than 500 kDa, less than 450 kDa, less than 400 kDa, less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, a "low molecular weight" bio-ink composition is utilized. In some such embodiments, the composition contains biopolymers within a molecular weight range between about 3.5 kDa and about 120 kDa. To give but one example, low molecular weight silk fibroin compositions, and methods of preparing such compositions as may be useful in the context of the present disclosure, are described in detail in U.S. provisional application 61/883,732, entitled "LOW MOLECULAR WEIGHT SILK FIBROIN AND USES THEREOF," the entire contents of which are incorporated herein by reference.

In some embodiments, bio-ink compositions for use in accordance with the present disclosure are substantially free of biopolymer components outside of a particular molecular weight range or threshold. For example, in some embodiments, a bio-ink composition is substantially free of biopolymer components having a molecular weight above about 400 kDa. In some embodiments, described biopolymer inks are substantially free of protein fragments over 200 kDa. "In some embodiments, the highest molecular weight biopolymers in provided bio-ink compositions have a molecular weight that is less than about 300 kDa-about 400 kDa (e.g., less than about 400 kDa, less than about 375 kDa, less than about 350 kDa, less than about 325 kDa, less than about 300 kDa, etc.).

In some embodiments, bio-ink compositions for use in accordance with the present disclosure are comprised of polymers (e.g., protein polymers) having molecular weights within the range of about 20 kDa-about 400 kDa, or within the range of about 3.5 kDa and about 120 kDa.

Those skilled in the art will appreciate that bio-ink compositions of a desired molecular weight (i.e., containing biopolymers within a particular molecular weight range and/or substantially free of biopolymers outside of that molecular weight range) may be prepared ab initio, or alternatively may be prepared either by fragmenting compositions of higher-molecular weight compositions, or by aggregating compositions of lower molecular weight polymers.

To give but one example, it is known in the art that different molecular weight preparations of silk fibroin polypeptides may be prepared or obtained by boiling silk solutions for different amounts of time. For example, established conditions (see, for example, Wray, et. al., 99 *J. Biomedical Materials Research Part B: Applied Biomaterials* 2011, which is hereby incorporated by reference in its entirety herein) are known to generate silk fibroin polypeptide compositions with maximal molecular weights in the range of about 300 kDa-about 400 kDa after about 5 minutes of boiling; compositions with molecular weights about 60 kDa are can be achieved under comparable conditions after about 60 minutes of boiling.

In some particular embodiments, silk fibroin polypeptide compositions of desirable molecular weight can be derived by degumming silk cocoons at or close to (e.g., within 5% of) an atmospheric boiling temperature, where such degumming involves at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, such degumming is performed at a temperature of: about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about at least 150° C.

In some particular embodiments, bio-ink compositions for use in accordance with the present disclosure is provided, prepared, and/or manufactured from a solution of silk fibroin that has been boiled for at least about 5, 10, 15, 20, 25, 30, 35, 40, 45, 50, 55, 60, 70, 80, 90, 100, 110, 120, 150, 180, 210, 240, 270, 310, 340, 370, 410 minutes or more. In some embodiments, such boiling is performed at a temperature within the range of: about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about at least 120° C. In some embodiments, such boiling is performed at a temperature below about 65° C. In some embodiments, such boiling is performed at a temperature of about 60° C. or less.

In some embodiments, one or more processing steps of a bio-ink composition for use in accordance with the present disclosure is performed at an elevated temperature relative to ambient temperature. In some embodiments, such an elevated temperature can be achieved by application of pressure. For example, in some embodiments, elevated temperature (and/or other desirable effectis) can be achieved or simulated through application of pressure at a level between about 10-40 psi, e.g., at about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

Concentration

In some embodiments, bio-ink compositions are prepared, provided, maintained and or utilized within a selected concentration range of biopolymer.

For example, in some embodiments, a bio-ink composition of interest may contain biopolymer (e.g., a polypeptide such as a silk fibroin polypeptide) at a concentration within the range of about 0.1 wt % to about 95 wt %, 0.1 wt % to about 75 wt %, or 0.1 wt % to about 50 wt %. In some embodiments, the aqueous silk fibroin solution can have silk fibroin at a concentration of about 0.1 wt % to about 10 wt %, about 0.1 wt % to about 5 wt %, about 0.1 wt % to about 2 wt %, or about 0.1 wt % to about 1 wt %. In some embodiments, the biopolymer is present at a concentration of about 10 wt % to about 50 wt %, about 20 wt % to about 50 wt %, about 25 wt % to about 50 wt %, or about 30 wt % to about 50 wt %. In some embodiments, a weight percent of silk in solution is about less than 1 wt %, is about less than 1.5 wt %, is about less than 2 wt %, is about less than 2.5 wt %, is about less than 3 wt %, is about less than 3.5 wt %, is about less than 4 wt %, is about less than 4.5 wt %, is about less than 5 wt %, is about less than 5.5 wt %, is about less than 6 wt %, is about less than 6.5 wt %, is about less than 7 wt %, is about less than 7.5 wt %, is about less than 8 wt %, is about less than 8.5 wt %, is about less than 9 wt %, is about less than 9.5 wt %, is about less than 10 wt %, is about less than 11 wt %, is about less than 12 wt %, is about less than 13 wt %, is about less than 14 wt %, is about less than 15 wt %, is about less than 16 wt %, is about less than 17 wt %, is about less than 18 wt %, is about less than 19 wt %, is about less than 20 wt %, is about less than 25 wt %, or is about less than 30 wt %.

In some particular embodiments, the present disclosure provides the surprising teaching that particularly useful bio-ink compositions with can be provided, preparedmaintained and/or utilized with a biopolymer concentratio that is less than about 10 wt %, or even that is about 5% wt %, about 4 wt %, about 3 wt %, about 2 wt %, about 1 wt % or less, particularly when the biopolymer is or comprises a silk biopolymer.

Degradation Properties of Silk-Based Materials

Additionally, as will be appreciated by those of skill in the art, much work has established that researchers have the ability to control the degradation process of silk. According to the present disclosure, such control can be particularly valuable in the fabrication of electronic components, and particularly of electronic components that are themselves and/or are compatible with biomaterials. Degradability (e.g., bio-degradability) is often essential for biomaterials used in tissue engineering and implantation. The present disclosure encompasses the recognition that such degradability is also relevant to and useful in the fabrication of silk electronic components.

According to the present disclosure, one particularly desirable feature of silk-based materials is the fact that they can be programmably degradable. That is, as is known in the art, depending on how a particular silk-based material is prepared, it can be controlled to degrade at certain rates. Degradability and controlled release of a substance from silk-based materials have been published (see, for example, WO 2004/080346, WO 2005/012606, WO 2005/123114, WO 2007/016524, WO 2008/150861, WO 2008/118133, each of which is incorporated by reference herein).

Control of silk material production methods as well as various forms of silk-based materials can generate silk compositions with known degradation properties. For example, using various silk fibroin materials (e.g., microspheres of approximately 2 μm in diameter, silk film, silk stents) entrapped agents such as therapeutics can be loaded in active form, which is then released in a controlled fashion, e.g., over the course of minutes, hours, days, weeks to months. It has been shown that layered silk fibroin coatings can be used to coat substrates of any material, shape and size, which then can be used to entrap molecules for controlled release, e.g., 2-90 days.

Crystalline Silk Materials

As known in the art and as described herein, silk proteins can stack with one another in crystalline arrays. Various properties of such arrays are determined, for example, by the degree of beta-sheet structure in the material, the degree of cross-linking between such beta sheets, the presence (or absence) of certain dopants or other materials. In some embodiments, one or more of these features is intentionally controlled or engineered to achieve particular characteristics of a silk matrix. In some embodiments, silk fibroin-based stents are characterized by crystalline structure, for example, comprising beta sheet structure and/or hydrogen bonding. In some embodiments, provided silk fibroin-based stents are characterized by a percent beta sheet structure within the range of about 0% to about 45%. In some embodiments, silk fibroin-based stents are characterized by crystalline structure, for example, comprising beta sheet structure of about 1%, about 2%, about 3%, about 4%, about 5%, about 6%, about 7%, about 8%, about 9%, about 10%, about 11%, about 12%, about 13%, about 1%, about 1%, about 1%, about 1%, about 1%, about 1%, about 1%, about 1%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, or about 45%.

Nanosized Crystalline Particles

In some embodiments, silk fibroin-based tracheal stents are characterized in that they include submicron size or nanosized crystallized spheres and/or particles. In some embodiments, such submicron size or nanosized crystallized spheres and/or particles have average diameters ranging between about 5 nm and 200 nm. In some embodiments, submicron size or nanosized crystallized spheres and/or particles have less than 150 nm average diameter, e.g., less than 145 nm, less than 140 nm, less than 135 nm, less than 130 nm, less than 125 nm, less than 120 nm, less than 115 nm, less than 110 nm, less than 100 nm, less than 90 nm, less than 80 nm, less than 70 nm, less than 60 nm, less than 50 nm, less than 40 nm, less than 30 nm, less than 20 nm, less than 15 nm, less than 10 nm, less than 5 nm, or smaller. In some preferred embodiments, submicron size or nanosized crystallized spheres and/or particles have average diameters of less than 100 nm.

Additives, Agents, and/or Functional Moieties

In some embodiments, a bulk material of a stent includes one or more (e.g., one, two, three, four, five or more) additives, agents, and/or functional moieties. Without wishing to be bound by a theory, additives, agents, and/or functional moieties can provide one or more desirable properties to the stent, e.g., strength, flexibility, ease of processing and handling, biocompatibility, bioresorbability, lack of air bubbles, surface morphology, and the like. In some embodiments, additives, agents, and/or functional moieties can be covalently or non-covalently linked with silk fibroin and can be integrated homogenously or heterogeneously within the bulk material. In some embodiments, the active agent is absorbed/adsorbed on a surface of the stent.

In some embodiments, additives, agents, and/or functional moieties can be in any physical form. For example, additives, agents, and/or functional moieties can be in the form of a particle (e.g., microparticle or nanoparticle), a fiber, a film, a gel, a mesh, a mat, a non-woven mat, a powder, a liquid, or any combinations thereof. In some embodiments, a silk fibroin tracheal stent comprising additives, agents, and/or functional moieties can be formulated by mixing one or more additives, agents, and/or functional moieties with a silk fibroin-fibroin solution used to make such a stent.

In some embodiments, an additives, agents, and/or functional moieties are covalently associated (e.g., via chemical modification or genetic engineering). In some embodiments, additives, agents, and/or functional moieties are non-covalently associated.

Without limitations, additives, agents, and/or functional moieties can be selected from the group consisting of anti-proliferative agents, biopolymers, nanoparticles (e.g., gold nanoparticles), proteins, peptides, nucleic acids (e.g., DNA, RNA, siRNA, modRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, enzymes, small molecules, antibiotics or antimicrobial compounds, toxins, therapeutic agents and prodrugs, small molecules and any combinations thereof.

In some embodiments, an additive, agent, or functional moiety is a polymer. In some embodiments, a polymer is a biocompatible polymer. As used herein, "biocompatible polymer" refers to any polymeric material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polylactic acid, polyglycolic acid, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described for example in U.S. Pat. Nos. 6,302,848; 6,395,734; 6,127,143; 5,263,992; 6,379,690; 5,015,476; 4,806,355; 6,372,244; 6,310,188; 5,093,489; 387,413; 6,325,810; 6,337,198; 6,267,776; 5,576,881; 6,245,537; 5,902,800; and 5,270,419, content of all of which is incorporated herein by reference.

In some embodiments, a biocompatible polymer is PEG or PEO. As used herein, term "polyethylene glycol" or "PEG" means an ethylene glycol polymer that contains about 20 to about 2000000 linked monomers, typically about 50-1000 linked monomers, usually about 100-300. PEG is also known as polyethylene oxide (PEO) or polyoxyethylene (POE), depending on its molecular weight. Generally PEG, PEO, and POE are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete PEGs are also available with different geometries.

As used herein, PEG is intended to be inclusive and not exclusive. In some embodiments, PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG With degradable linkages therein. Further, a PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)m in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as biocompatible polymers.

Some exemplary PEGs include, but are not limited to, PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG15000, PEG 20000, PEG250000, PEG500000, PEG100000, PEG2000000 and the like. In some embodiments, PEG is of MW 10,000 Dalton. In some embodiments, PEG is of MW 100,000, i.e. PEO of MW 100,000.

In some embodiments, a polymer is a biodegradable polymer. As used herein, "biodegradable" describes a material which can decompose under physiological conditions into breakdown products. Such physiological conditions include, for example, hydrolysis (decomposition via hydrolytic cleavage), enzymatic catalysis (enzymatic degradation), and mechanical interactions. As used herein, "biodegradable" also encompasses "bioresorbable", which describes a substance that decomposes under physiological conditions to break down to products that undergo bioresorption into the host-organism, namely, become metabolites of the biochemical systems of the host organism.

As used herein, "bioresorbable" and "bioresorption" encompass processes such as cell-mediated degradation, enzymatic degradation and/or hydrolytic degradation of the bioresorbable polymer, and/or elimination of the bioresorbable polymer from living tissue as will be appreciated by the person skilled in the art.

"Biodegradable polymer", as used herein, refers to a polymer that at least a portion thereof decomposes under physiological conditions. A polymer can thus be partially decomposed or fully decomposed under physiological conditions.

Exemplary biodegradable polymers include, but are not limited to, polyanhydrides, polyhydroxybutyric acid, polyorthoesters, polysiloxanes, polycaprolactone, poly(lactic-co-glycolic acid), poly(lactic acid), poly(glycolic acid), and copolymers prepared from the monomers of these polymers.

In some embodiments, additives, agents, or functional moieties include a bioinert material. As used herein, a "bioinert" material refers to any material that once placed in vivo has minimal interaction with its surrounding tissue. Exemplary bioinert materials include, but are not limited to, gold, stainless steel, titanium, alumina, partially stabilized zirconia, and ultra-high molecular weight polyethylene.

In some embodiments, additives, agents, or functional moieties can be a silk fibroin particle or powder. Various methods of producing silk fibroin particles (e.g., nanoparticles and microparticles) are known in the art. See for example, PCT Publication No. WO 2011/041395 and No. WO 2008/118133; U.S. App. Pub. No. U.S. 2010/0028451; U.S. Provisional Application Ser. No. 61/719,146, filed Oct. 26, 2012; and Wenk et al. J Control Release, Silk fibroin spheres as a platform for controlled drug delivery, 2008; 132: 26-34, content of all of which is incorporated herein by reference in their entirety.

In some embodiments, additives, agents, or functional moieties include silk fibroin fiber. In some embodiments, silk fibroin fibers could be chemically attached by redissolving part of the fiber in HFIP and attaching to stent. Use of silk fibroin fibers is described in, for example, US patent application publication no. US20110046686, content of which is incorporated herein by reference.

In some embodiments, silk fibroin fibers are microfibers or nanofibers. In some embodiments, additives, agents, or functional moieties are micron-sized silk fibroin fiber (10-600 μm). Micron-sized silk fibroin fibers can be obtained by hydrolyzing degummed silk fibroin or by increasing a boiling time of a degumming process. Alkali hydrolysis of silk fibroin to obtain micron-sized silk fibroin fibers is described for example in Mandal et al., PNAS, 2012, doi: 10.1073/pnas.1119474109; U.S. Provisional Application No. 61/621,209, filed Apr. 6, 2012; and PCT application no. PCT/US13/35389, filed Apr. 5, 2013, content of all of which is incorporated herein by reference. Because regenerated silk fibroin fibers made from HFIP silk fibroin solutions are mechanically strong. the regenerated silk fibroin fibers can also be used as additive.

In some embodiments, silk fibroin fiber is an unprocessed silk fibroin fiber unprocessed silk fibroin fiber is meant silk fibroin, obtained directly from the silk fibroin gland. When silk fibroin, obtained directly from the silk fibroin gland, is allowed to dry, the structure is referred to as silk fibroin I in the solid state. Thus, an unprocessed silk fibroin fiber includes silk fibroin mostly in the silk fibroin I conformation. A regenerated or processed silk fibroin fiber on the other hand includes silk fibroin having a substantial silk fibroin II or beta-sheet crystallinity.

In some embodiments, a conformation of the fibroin in a stent can be altered before, during or after its formation. Induced conformational change alters silk fibroin crystallinity, e.g., Silk fibroin II beta-sheet crystallinity. Without wishing to be bound by a theory, it is believed that degradation of the bulk material or optional release of an additive (e.g., an active agent) from the bulk material varies with the beta-sheet content of the silk fibroin. Conformational change can be induced by any methods known in the art, including, but not limited to, alcohol immersion (e.g., ethanol, methanol), water annealing, shear stress (e.g., by vortexing), ultrasound (e.g., by sonication), pH reduction (e.g., pH titration and/or exposure to an electric field) and any combinations thereof. For example, a conformational change can be induced by one or more methods, including but not limited to, controlled slow drying (Lu et al., 10 Biomacromolecules 1032 (2009)); water annealing (Jin et al., Water-Stable Silk fibroin Films with Reduced β-Sheet Content, 15 Adv. Funct. Mats. 1241 (2005); Hu et al. Regulation of Silk fibroin Material Structure by Temperature-Controlled Water Vapor Annealing, 12 Biomacromolecules 1686 (2011)); stretching (Demura & Asakura, Immobilization of glucose oxidase with Bombyx mori silk fibroin by only stretching treatment and its application to glucose sensor, 33 Biotech & Bioengin. 598 (1989)); compressing; solvent immersion, including methanol (Hofmann et al., Silk fibroin as an organic polymer for controlled drug delivery, 111 J Control Release. 219 (2006)), ethanol (Miyairi et al., Properties of b-glucosidase immobilized in sericin membrane. 56 J. Fermen. Tech. 303 (1978)), glutaraldehyde (Acharya et al., Performance evaluation of a silk fibroin protein-based matrix for the enzymatic conversion of tyrosine to L-DOPA. 3 Biotechnol J. 226 (2008)), and 1-ethyl-3-(3-dimethyl aminopropyl) carbodiimide (EDC) (Bayraktar et al., Silk fibroin as a novel coating material for controlled release of theophylline. 60 Eur J Pharm Biopharm. 373 (2005)); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Content of all of the references listed above is incorporated herein by reference in their entirety.

In some embodiments, an additive, agent, and/or functional moiety is a plasticizer. As used herein, a "plasticizer" is intended to designate a compound or a mixture of compounds that can increase flexibility, processability and extensibility of the polymer in which it is incorporated. In some embodiments, a plasticizer can reduce the viscosity of the melt, lower the second order transition temperatures and the elastic modulus of the product. In some embodiments, suitable plasticizers include, but are not limited to, low molecular weight polyols having aliphatic hydroxyls such as ethylene glycol; propylene glycol; propanetriol (i.e., glycerol); glyceryl monostearate; 1,2-butylene glycol; 2,3-butylene glycol; styrene glycol; polyethylene glycols such as diethylene glycol, triethylene glycol, tetraethylene glycol and other polyethylene glycols having a molecular weight of about 1,000 or less; polypropylene glycols of molecular weight 200 or less; glycol ethers such as monopropylene glycol monoisopropyl ether; propylene glycol monoethyl ether; ethylene glycol monoethyl ether; diethylene glycol monoethyl ether; ester-type plasticizers such as sorbitol lactate, ethyl lactate, butyl lactate, ethyl glycolate, allyl glycolate; and amines such as monoethanolamine, diethanolamine, triethanolamine, monisopropanolamine, triethylenetetramine, 2-amino-2-methyl-1,3-propanediol, polymers and the like. In one embodiment, the plasticizer can include glycerol.

In some embodiments, plasticizers may be included in a silk formulation to augment properties or add new functionality. In some embodiments, an addition of 1-50% glycerol increased elasticity and compliance of such a stent. Specifically, a glycerol concentration of 5-10% by weight is most advantageous mechanical properties for this application. Lower concentrations of glycerol do no result in a detectable increase in elasticity, while higher concentrations compromise the stiffness of the stents. In some embodiments, glycerol is diluted with deionized water before being added to the silk solution. In some embodiments, glycerol solution concentrations of 350 mg/mL or lower, may induce gelation when added to silk. In some embodiments, such concentrations makes it nearly impossible to homogenize a solution, and to add in an accurate amount of glycerol. In some embodiments, a glycerol solution concentration of 700 mg/mL is preferred. In some embodiments, once added, a silk/glycerol solution is mixed by gentle inversion, aggressive sonication or vortex mixing can cause preemptive gelation.

In some embodimnts, provided silk fibroin tracheal stents include additives, agents, and/or functional moieties, for example, therapeutic, preventative, and/or diagnostic agents.

In some embodiments, a therapeutic agent can be selected from the group consisting of anti-infectives, chemotherapeutic agents, anti-rejection agents, analgesics and analgesic combinations, anti-inflammatory agents, hormones, growth factors, antibiotics, antiviral agents, steroids, bone morphogenic proteins, bone morphogenic-like proteins, epidermal growth factor, fibroblast growth factor, platelet derived growth factor (PDGF), insulin-like growth factor, transforming growth factors, vascular endothelial growth factor, and any combinations thereof.

In some embodiments, an additive is or includes one or more therapeutic agents. In general, a therapeutic agent is or includes a small molecule and/or organic compound with pharmaceutical activity (e.g., activity that has been demonstrated with statistical significance in one or more relevant pre-clinical models or clinical settings). In some embodiments, a therapeutic agent is a clinically-used drug. In some embodiments, a therapeutic agent is or includes an cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, an additive, agent, and/or functional moiety is a therapeutic agent. A "therapeutic agent" refers to a biological or chemical agent used for treating, curing, mitigating, or preventing deleterious conditions in a subject. "Therapeutic agent" also includes substances and agents for combating a disease, condition, or disorder of a subject, and includes drugs, diagnostics, and instrumentation. "Therapeutic agent" also includes anything used in medical diagnosis, or in restoring, correcting, or modifying physiological functions. "Therapeutic agent" and "pharmaceutically active agent" are used interchangeably herein.

A therapeutic agent is selected according to the treatment objective and biological action desired. General classes of therapeutic agents include anti-microbial agents such as adrenergic agents, antibiotic agents or antibacterial agents, antiviral agents, anthelmintic agents, anti-inflammatory agents, antineoplastic agents, antioxidant agents, biological reaction inhibitors, botulinum toxin agents, chemotherapy agents, contrast imaging agents, diagnostic agents, gene therapy agents, hormonal agents, mucolytic agents, radioprotective agents, radioactive agents including brachytherapy materials, tissue growth inhibitors, tissue growth enhancers, and vasoactive agents. Therapeutic agent can be selected from any class suitable for the therapeutic objective. In some embodiments, a therapeutic agent is an antithrombotic or fibrinolytic agent selected from the group consisting of anticoagulants, anticoagulant antagonists, antiplatelet agents, thrombolytic agents, thrombolytic agent antagonists, and any combinations thereof.

In some embodiments, a therapeutic agent is thrombogenic agent selected from the group consisting of thrombolytic agent antagonists, anticoagulant antagonists, pro-coagulant enzymes, pro-coagulant proteins, and any combinations thereof. Some exemplary thrombogenic agents include, but are not limited to, protamines, vitamin K1, amiocaproic acid (amicar), tranexamic acid (amstat), anagrelide, argatroban, cilstazol, daltroban, defibrotide, enoxaparin, fraxiparine, indobufen, lamoparan, ozagrel, picotamide, plafibride, tedelparin, ticlopidine, triflusal, collagen, and collagen-coated particles.

In some embodiments, a therapeutic agent is a vasodilator. A vasodilator can be selected from the group consisting of alpha-adrenoceptor antagonists (alpha-blockers), agiotensin converting enzyme (ACE) inhibitors, angiotensin receptor blockers (ARBs), beta2-adrenoceptor agonists (β2-agonists), calcium-channel blockers (CCBs), centrally acting sympatholytics, direct acting vasodilators, endothelin receptor antagonists, ganglionic blockers, nitrodilators, phosphodiesterase inhibitors, potassium-channel openers, renin inhibitors, and any combinations thereof. Exemplary vasodilator include, but are not limited to, prazosin, terazosin, doxazosin, trimazosin, phentolamine, phenoxybenzamine, benazepril, captopril, enalapril, fosinopril, lisinopril, moexipril, quinapril, ramipril, candesartan, eprosartan, irbesartan, losartan, olmesartan, telmisartan, valsartan, Epinephrine, Norepinephrine, Dopamine, Dobutamine, Isoproterenol, amlodipine, felodipine, isradipine, nicardipine, nifedipine, nimodipine, nitrendipine, clonidine, guanabenz, guanfacine, α-methyldopa, hydralazine, Bosentan, trimethaphan camsylate, isosorbide dinitrate, isosorbide mononitrate, nitroglycerin, erythrityl tetranitrate, pentaerythritol tetranitrate, sodium nitroprusside, milrinone, inamrinone (formerly amrinone), cilostazol, sildenafil, tadalafil, minoxidil, aliskiren, nitric oxide, sodium nitrite, nitroglycerin, and analogs, derivatives, prodrugs, and pharmaceutically acceptable salts thereof.

Exemplary pharmaceutically active compound include, but are not limited to, those found in *Harrison's Principles of Internal Medicine,* 13th Edition, Eds. T. R. Harrison et al. McGraw-Hill N.Y., NY; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

In some embodiments, active agents can be selected from small organic or inorganic molecules; saccharines; oligosaccharides; polysaccharides; biological macromolecules; peptides; proteins; peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. The active agent can be hydrophobic, hydrophilic, or amphiphilic.

Small molecules can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is highly preferred that a small molecule have a molecular mass equal to or less than 700 Daltons.

In some embodiments, possible additives, agents, or functional moieties are soluble drugs that could be released into a local environment as the stent degrades, growth factors to stimulate local tissue regeneration, cell adhesion proteins to promote cellular infiltration, cleavable crosslinkers to further control degradation, or patient derived cells.

In some embodiments, a stent includes a biologically active agent. As used herein, "biological activity" or "bioactivity" refers to the ability of a molecule or composition to affect a biological sample. Biological activity can include, without limitation, elicitation of a stimulatory, inhibitory, regulatory, toxic or lethal response in a biological assay. For example, a biological activity can refer to the ability of a compound to modulate the effect/activity of an enzyme, block a receptor, stimulate a receptor, modulate the expression level of one or more genes, modulate cell proliferation, modulate cell division, modulate cell morphology, or any combination thereof. In some instances, a biological activity can refer to the ability of a compound to produce a toxic effect in a biological sample. A stent including an active agent can be formulated by mixing one or more active agents with the silk fibroin-fibroin solution used to make the stent.

Examples of biologically active compounds include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard, Cell Mol Life Sci. 2003, 60(1):119-32 and Hersel U. et al., Biomaterials, 2003, 24(24):4385-415); YIGSR peptides; biologically active ligands; and substances that enhance or exclude particular varieties of cellular or tissue ingrowth.

In some embodiments, an active agent is an anti-restenosis or restenosis inhibiting agent. Suitable anti-restenosis agents include: (1) antiplatelet agents including: (a) thrombin inhibitors and receptor antagonists, (b) adenosine disphosphate (ADP) receptor antagonists (also known as purinoceptor$_1$ receptor antagonists), (c) thromboxane inhibitors and receptor antagonists and (d) platelet membrane glycoprotein receptor antagonists; (2) inhibitors of cell adhesion molecules, including (a) selectin inhibitors and (b) integrin inhibitors; (3) anti-chemotactic agents; (4) interleukin receptor antagonists (which also serve as anti-pain/anti-inflammation agents); and (5) intracellular signaling inhibitors including: (a) protein kinase C (PKC) inhibitors and protein tyrosine kinase inhibitors, (b) modulators of intracellular protein tyrosine phosphatases, (c) inhibitors of src homology$_2$ (SH2) domains, and (d) calcium channel antagonists. Exemplary specific restenosis-inhibiting agents include microtubule stabilizing agents such as rapamycin, mitomycin C, TAXOL®, paclitaxel (i.e., paclitaxel, paxlitaxel analogs, or paclitaxel derivatives, and mixtures thereof). For example, derivatives suitable for use in the stent include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

In some embodiments, an active agent is an anti-coagulation agent. As used herein, "anti-coagulation agent" refers to any molecule or composition that promotes blood coagulation or activates the blood coagulation cascade or a portion thereof. Exemplary anti-coagulation agents include, for example, phospholipids such as, e.g., negatively charged phospholipids; lipoproteins such as, e.g., thromboplastin, and the like; proteins such as tissue factor, activated serin proteases such as Factors IIa (thrombin), VII, VIIa, VIII, IX, IXa, Xa, XIa, XII, XIIa, von Willebrand factor (vWF), protein C, snake venoms such as PROTAC® enzyme, Ecarin, Textarin, Noscarin, Batroxobin, Thrombocytin, Russell's viper venom (RVV), and the like; polyvalent cations; calcium ions; tissue factor; silica; kaolin; bentonite; diatomaceous earth; ellagic acid; celite; and any mixtures thereof.

In some embodiments, provided stents include for example, antibiotics. Antibiotics suitable for incorporation in stents include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridine, cephalothin, moxalactam, piperacillin, ticarcillin and combination thereof.

In some embodiments, provided stents include for example, anti-inflammatories. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, additives, agents, and/or functional moieties include a nitric oxide or a prodrug thereof.

In some embodiments, provided stents include, for example, polypeptides (e.g., proteins), including but are not limited to: one or more antigens, cytokines, hormones, chemokines, enzymes, and any combination thereof as an agent and/or functional group. Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

In some embodiments, provided stents include, for example, antibodies. Suitable antibodies for incorporation in stents include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, an active agent is an enzyme that hydrolyzes silk fibroin. Without wishing to be bound by a theory, such enzymes can be used to control degradation of a stent after implantation into a subject. Controlled degradation of silk fibroin-fibroin based scaffolds with enzymes embedded therein is described in, for example, U.S. Provisional Application No. 61/791,501, filed Mar. 15, 2013, content of which is incorporated herein by reference in its entirety.

In some embodiments, the bulk material of the stent can include a cell. Stent with the bulk material comprising a cell can be used for organ repair, organ replacement or regeneration. Cells amenable to be incorporated into the composition include, but are not limited to, stem cells (embryonic stem cells, mesenchymal stem cells, neural stem cells, bone-marrow derived stem cells, hematopoietic stem cells, and induced pluripotent stem cells); pluripotent cells; chrondrocytes progenitor cells; pancreatic progenitor cells; myoblasts; fibroblasts; chondrocytes; keratinocytes; neuronal cells; glial cells; astrocytes; pre-adipocytes; adipocytes; vascular endothelial cells; hair follicular stem cells; endothelial progenitor cells; mesenchymal cells; smooth muscle progenitor cells; osteocytes; parenchymal cells such as hepatocytes; pancreatic cells (including Islet cells); cells of intestinal origin; and combination thereof, either as obtained from donors, from established cell culture lines, or even before or after molecular genetic engineering. Without limitations, the cells useful for incorporation into the composition can come from any source, for example human, rat or mouse. In some embodiments, the cell can from a subject into which the stent is to be implanted.

In some embodiments, a cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

In some embodiments, differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science,* 2007, 318, 1917-1920 and Takahashi K. et. al., Cell, 2007, 131, 1-12).

In some embodiments, when using a stent with cells, it can be desirable to add other materials to promote the growth, differentiation or proliferation of the cell. Exemplary materials known to promote cell growth include, but not limited to, cell growth media, such as Dulbecco's Modified Eagle Medium (DMEM), fetal bovine serum (FBS), non-essential amino acids and antibiotics, and growth and morphogenic factors such as fibroblast growth factor (e.g., FGF 1-9), transforming growth factors (TGFs), vascular endothelial growth factor (VEGF), epidermal growth factor (EGF), platelet derived growth factor (PDGF), insulin-like growth factor (IGF-I and IGF-II), bone morphogenetic growth factors (e.g., BMPs 1-7), bone morphogenetic-like proteins (e.g., GFD-5, GFD-7, and GFD-8), transforming growth factors (e.g., TGF-α, TGF-βI-III), nerve growth factors, and related proteins. Growth factors are known in the art, see, e.g., Rosen & Thies, CELLULAR & MOL. BASIS BONE FORMATION & REPAIR (R.G. Landes Co.).

In some embodiments, cells suitable for use herein include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

In some embodiments, provided stents include, for example, organisms, such as, a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

In some embodiments, provided stents include, for example, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

In some embodiments, provided stents include, for example, an optically or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

Without wishing to be bound by a theory, incorporating an active agent in a bulk material of a stent enables delivery of an active agent in a controlled released manner. Maintaining an active agent in an active form throughout in the silk fibroin-fibroin matrix enables it to be active upon release from the stent. Controlled release of active agent permits active agent to be released sustainably over time, with controlled release kinetics. In some embodiments, an active agent is delivered continuously to the site where treatment is needed, for example, over several weeks. Controlled release over time, for example, over several days or weeks, or longer, permits continuous delivery of the bioactive agent to obtain preferred treatments. In some embodiments, controlled delivery is advantageous because it protects bioactive agents from degradation in vivo in body fluids and tissue, for example, by proteases.

Controlled release of an active agent from the stent can be designed to occur over time, for example, over 12 hours or 24 hours. Time of release may be selected, for example, to occur over a time period of about 12 hours to 24 hours; about 12 hours to 42 hours; or, e.g., about 12 to 72 hours. In another embodiment, release can occur for example on the order of about 1 day to 15 days. Controlled release time can be selected based on the condition treated. For example, longer times can be more effective for wound healing, whereas shorter delivery times can be more useful for some cardiovascular applications.

Controlled release of an active agent from a stent in vivo can occur, for example, in the amount of about 1 ng to 1 mg/day. In some embodiments, controlled release can occur in the amount of about 50 ng to 500 ng/day, about 75 ng to 250 ng/day, about 100 ng to 200 ng/day, or about 125 ng to 175 ng/day.

In some embodiments, provided silk fibroin tracheal stents include additives, agents, and/or functional moieties at a total amount from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, provided silk fibroin tracheal stents include additives, agents, and/or functional moieties at a molar ratio relative to polymer (i.e., a polymer:additive ratio) of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, moiety polymer:additive ratio is, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, moiety polymer:additive ratio is, e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, a ratio of silk fibroin to a total amount of additive, agent, and/or functional moiety in a bulk material can range from 100:1 to 1:100. For example, the ratio of silk fibroin to additive can range from 50:1 to 1:50, from 25:1 to 1:25, from 20:1 to 1: 20, from 15:1 to 1:15, from 10:1 to 1:10, or from 5:1 to 1:5. In some embodiments, a ratio of silk fibroin to additive, agent, and/or functional moiety can be from 5:1 to 1:1. In one embodiment, a ratio of silk fibroin to additive, agent, and/or functional moiety can be 3:1. A ratio can be molar ratio, weight ratio, or volume ratio.

A total amount of active agent in a bulk material can be from about 0.1 wt % to about 0.99 wt %, from about 0.1 wt % to about 70 wt %, from about 5 wt % to about 60 wt %, from about 10 wt % to about 50 wt %, from about 15 wt % to about 45 wt %, or from about 20 wt % to about 40 wt %, of a total weight of bulk material.

Nucleic Acids

In some embodiments, provided stents include additives, for example, nucleic acid agents. In some embodiments, a stent may release nucleic acid agents. In some embodiments, a nucleic acid agent is or includes a therapeutic agent. In some embodiments, a nucleic acid agent is or includes a diagnostic agent. In some embodiments, a nucleic acid agent is or includes a prophylactic agent.

It would be appreciate by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or include deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or includes at least one protein-coding element. In some embodiments, a nucleic acid has a nucleotide sequence that is or includes at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc.). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc.) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiments, a nucleic acid agent is or includes an oligonucleotide. In some embodiments, a nucleic acid agent is or includes an antisense oligonucleotide. Nucleic acid agents may include a chemical modification at the individual nucleotide level or at the oligonucleotide backbone level, or it may have no modifications.

In some embodiments of the present disclosure, a nucleic acid agent is an siRNA agent. Short interfering RNA (siRNA) includes an RNA duplex that is approximately 19 basepairs long and optionally further includes one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to include sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase 1B (PTP1B).

Growth Factor

In some embodiments, provided stents include additives, for example, growth factor. In some embodiments, a stent may release growth factor. In some embodiments, a stent may release multiple growth factors. In some embodiments growth factor known in the art include, for example, adrenomedullin, angiopoietin, autocrine motility factor, basophils, brain-derived neurotrophic factor, bone morphogenetic protein, colony-stimulating factors, connective tissue growth factor, endothelial cells, epidermal growth factor, erythropoietin, fibroblast growth factor, fibroblasts, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, keratinocytes, lymphocytes, macrophages, mast cells, myostatin, nerve growth factor, neurotrophins, platelet-derived growth factor, placenta growth factor, osteoblasts, platelets, proinflammatory, stromal cells, T-lymphocytes, thrombopoietin, transforming growth factor alpha, transforming growth factor beta, tumor necrosis factor-alpha, vascular endothelial growth factor and combinations thereof.

In some embodiments, provided stents include additives, for example, that are particularly useful for healing. Exemplary agents useful as growth factor for defect repair and/or healing can include, but are not limited to, growth factors for defect treatment modalities now known in the art or later-developed; exemplary factors, agents or modalities including natural or synthetic growth factors, cytokines, or modulators thereof to promote bone and/or tissue defect healing. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), Derma-SIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that includes both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox®) lipoic acid, nitric oxide synthase3, matrix metalloproteinase 9 (MMP-9), CCT-ETA, alphav-beta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that agents useful for growth factor for healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

In some embodiments, the active agent is a growth factor or cytokine. A non-limiting list of growth factors and cytokines includes, but is not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-la, IL-1(3, IL-6, IL-7, IL-8, IL-11, and IL-13, colony-stimulating factors, thrombopoietin, erythropoietin, fit3-ligand, and tumor necrosis factors (TNFα and TNFβ). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, PA: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In some embodiments, the active agent can be selected from anti-infectives such as antibiotics and antiviral agents; chemotherapeutic agents (i.e. anticancer agents); anti-rejection agents; anti-proliferative agents; analgesics and analgesic combinations; anti-inflammatory agents; erythropoietin (EPO); interferon α and γ; interleukins; tumor necrosis factor α and β; insulin, antibiotics; adenosine; cytokines; integrins; selectins; cadherins; insulin; hormones such as steroids; cytotoxins; prodrugs; immunogens; or lipoproteins.

In some embodiments, provided stents include additives, for example, that are particularly useful as diagnostic agents. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MM include gadolinium chelates, as well as iron, magnesium, manganese, copper, and chromium. Examples of materials useful for CAT and x-ray imaging include iodine-based materials.

In some embodiments, provided stents include additives, for example, radionuclides that are particularly useful as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming thermally-responsive conjugates in accordance with the invention include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Pb, $^{109}$Pd, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F. In some embodiments, a diagnostic agent may be a fluorescent, luminescent, or magnetic moiety.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication No.: 2004/0067503; Valeur, B., "Molecular Fluorescence: Principles and Applications," John Wiley and Sons, 2002; *Handbook of Fluorescent Probes and Research Products*, Molecular Probes, 9$^{th}$ edition, 2002; and *The Handbook—A Guide to Fluorescent Probes and Labeling Technologies*, Invitrogen, 10$^{th}$ edition, available at the Invitrogen web site; both of which are incorporated herein by reference).

REFERENCES

1. Cao, H., Liu, T. & Chew, S. Y. The application of nanofibrous scaffolds in neural tissue engineering. *Adv. Drug Deliv. Rev.* 61, 1055-1064 (2009).

2. Li, W.-J. & Tuan, R. S. Fabrication and application of nanofibrous scaffolds in tissue engineering. *Curr. Protoc. Cell Biol. Editor. Board Juan Bonifacino Al* Chapter 25, Unit 25.2 (2009).

3. Liang, D., Hsiao, B. S. & Chu, B. Functional electrospun nanofibrous scaffolds for biomedical applications. *Adv. Drug Deliv. Rev.* 59, 1392-1412 (2007).

4. Liu, X., Jin, X. & Ma, P. X. Nanofibrous hollow microspheres self-assembled from star-shaped polymers as injectable cell carriers for knee repair. *Nat. Mater.* 10, 398-406 (2011).

5. Xu, C. Y., Inai, R., Kotaki, M. & Ramakrishna, S. Aligned biodegradable nanofibrous structure: a potential scaffold for blood vessel engineering. *Biomaterials* 25, 877-886 (2004).

6. Chen, S. et al. Electrospun carbon fiber mat with layered architecture for anode in microbial fuel cells. *Electrochem. Commun.* 13, 1026-1029 (2011).

7. Hou, H. et al. Electrospun Polyacrylonitrile Nanofibers Containing a High Concentration of Well-Aligned Multiwall Carbon Nanotubes. *Chem. Mater.* 17, 967-973 (2005).

8. Inagaki, M., Yang, Y. & Kang, F. Carbon Nanofibers Prepared via Electrospinning. *Adv. Mater.* 24, 2547-2566 (2012).

9. Zhang, L., Lou, J. & Tong, L. Micro/nanofiber optical sensors. *Photonic Sens.* 1, 31-42 (2010).

10. Wang, P., Wang, Y. & Tong, L. Functionalized polymer nanofibers: a versatile platform for manipulating light at the nanoscale. *Light Sci. Appl.* 2, e102 (2013).

11. Liu, H., Edel, J. B., Bellan, L. M. & Craighead, H. G. Electrospun Polymer Nanofibers as Subwavelength Optical Waveguides Incorporating Quantum Dots. *Small* 2, 495-499 (2006).

12. Yang, M. et al. Ca2+-induced self-assembly of Bombyx mori silk sericin into a nanofibrous network-like protein matrix for directing controlled nucleation of hydroxylapatite nano-needles. *J. Mater. Chem. B* 3, 2455-2462 (2015).

13. Hsu, L.-H. et al. Nanofibrous hydrogels self-assembled from naphthalene diimide (NDI)/amino acid conjugates. *RSC Adv.* 5, 20410-20413 (2015).

14. Pisignano, D. et al. Polymer nanofibers by soft lithography. *Appl. Phys. Lett.* 87, 123109 (2005).

15. Park, M., Im, J., Park, J. & Jeong, U. Micropatterned Stretchable Circuit and Strain Sensor Fabricated by Lithography on an Electrospun Nanofiber Mat. *ACS Appl. Mater. Interfaces* 5, 8766-8771 (2013).

16. Shi, J., Wang, L. & Chen, Y. Microcontact Printing and Lithographic Patterning of Electrospun Nanofibers. *Langmuir* 25, 6015-6018 (2009).

17. Hahn, M. S. et al. Photolithographic patterning of polyethylene glycol hydrogels. *Biomaterials* 27, 2519-2524 (2006).

18. Xu, S. et al. Assembly of micro/nanomaterials into complex, three-dimensional architectures by compressive buckling. *Science* 347, 154-159 (2015).

19. Sydney Gladman, A., Matsumoto, E. A., Nuzzo, R. G., Mahadevan, L. & Lewis, J. A. Biomimetic 4D printing. *Nat. Mater.* 15, 413-418 (2016).

20. Qi, Y. et al. Piezoelectric Ribbons Printed onto Rubber for Flexible Energy Conversion. *Nano Lett.* 10, 524-528 (2010).

21. Khang, D.-Y. et al. Molecular Scale Buckling Mechanics in Individual Aligned Single-Wall Carbon Nanotubes on Elastomeric Substrates. *Nano Lett.* 8, 124-130 (2008).

22. Syms, R. R. A., Yeatman, E. M., Bright, V. M. & Whitesides, G. M. Surface tension-powered self-assembly of microstructures—the state-of-the-art. *J. Microelectromechanical Syst.* 12, 387-417 (2003).

23. Srinivasan, U., Liepmann, D. & Howe, R. T. Microstructure to substrate self-assembly using capillary forces. *J. Microelectromechanical Syst.* 10, 17-24 (2001).

24. Mastrangeli, M. et al. Self-assembly from milli- to nanoscales: methods and applications. *J. Micromechanics Microengineering* 19, 83001 (2009).

25. Harsh, K. F., Bright, V. M. & Lee, Y. C. Solder self-assembly for three-dimensional microelectromechanical systems. *Sens. Actuators Phys.* 77, 237-244 (1999).

26. Akiyama, T., Collard, D. & Fujita, H. Scratch drive actuator with mechanical links for self-assembly of three-dimensional MEMS. *J. Microelectromechanical Syst.* 6, 10-17 (1997).

27. Kambe, Y., Kojima, K., Tamada, Y., Tomita, N. & Kameda, T. Silk fibroin sponges with cell growth-promoting activity induced by genetically fused basic fibroblast growth factor. *J. Biomed. Mater. Res. A* 104, 82-93 (2016).

28. Kim, S. et al. Silk inverse opals. *Nat. Photonics* 6, 818-823 (2012).

29. Partlow, B. P. et al. Highly Tunable Elastomeric Silk Biomaterials. *Adv. Funct. Mater.* 24, 4615-4624 (2014).

30. Kim, U.-J. et al. Structure and properties of silk hydrogels. *Biomacromolecules* 5, 786-792 (2004).

31. Rockwood, D. N. et al. Materials fabrication from Bombyx mori silk fibroin. *Nat. Protoc.* 6, 1612-1631 (2011).

32. Perry, H., Gopinath, A., Kaplan, D. L., Dal Negro, L. & Omenetto, F. G. Nano- and Micropatterning of Optically Transparent, Mechanically Robust, Biocompatible Silk Fibroin Films. *Adv. Mater.* 20, 3070-3072 (2008).

33. Nogueira, G. M. et al. Preparation and characterization of ethanol-treated silk fibroin dense membranes for biomaterials application using waste silk fibers as raw material. *Bioresour. Technol.* 101, 8446-8451 (2010).

34. Chen, X., Shao, Z., Knight, D. P. & Vollrath, F. Conformation transition kinetics of Bombyx mori silk protein. *Proteins* 68, 223-231 (2007).

35. Lin, Y. et al. Tuning Chemical and Physical Crosslinks in Silk Electrogels for Morphological Analysis and Mechanical Reinforcement. *Biomacromolecules* 14, 2629-2635 (2013).

36. Mitropoulos, A. N. et al. Transparent, Nanostructured Silk Fibroin Hydrogels with Tunable Mechanical Properties. *ACS Biomater. Sci. Eng.* 1, 964-970 (2015).

37. Fernandes, H., Zhang, H. & Maldague, X. An active infrared thermography method for fiber orientation assessment of fiber-reinforced composite materials. *Infrared Phys. Technol.* 72, 286-292 (2015).

EXEMPLIFICATION

Unless otherwise specified, the examples provided herein were achieved using the following materials and/or methods:

Example 1

The present Example describes mold fabrication.

SU-8 2002 (Microchem) was initially spun onto silicon wafers to facilitate adhesion of thicker SU-8 layers to the underlying substrate. SU-8 2100 was then spun on substrates to desired thickness and processed under standard protocols (see data sheet). For multilayer molds, an initial SU-8 2100 layer was defined via exposure, and hard-baked. A second layer SU-8 2100 layer was subsequently spun and the substrate was then processed under standard protocols. Substrates were silanized via vapor deposition of trichloro(1H,1H,2H,2H-perfluorooctyl)silane (Sigma) in a vacuum chamber. Polydimethylsiloxane (Fisher) was subsequently poured onto molds and degassed to remove air bubbles. PDMS was baked overnight at 60 C, removed from molds, and allowed to crosslink to completion at 90 C over 24 hours.

Example 2

The present Example describes silk hydrogel formulations.

Silk fibroin (30 minute boil) was generated using established protocols forming an 8% silk stock solution. Silk was diluted to desired concentration (1%, 3% or 5%). Unless directly noted in the text, silk hydrogel was generated using 3% solution. Optionally, silk was doped with gold nanoparticles, multi-walled carbon nanotubes (25% weight ratio, US Nano—20 nm diameter/25 um long), or polyacrylic acid (1% weight ratio, Sigma). For fluorescent silk fibroin, 5 uL of 10 mg mL-1 stock solution of rhodamine-NHS (Invitrogen) in DMSO was added 5 mL of silk solution. Silk fibroin was crosslinked using 10 U mL-1 of horseradish peroxidase (Sigma), and 1% hydrogen peroxide (Sigma).

Example 3

The present Example describes formation of nanofibrillar structure.

PDMS molds were exposed to oxygen plasma (100 W, 60 s) to render substrates hydrophilic. Silk hydrogel solution was subsequently infiltrated into molded channels, and gelled in a humidified chamber over 6 hours. Patterned hydrogel was then subjected to mixtures of ethanol and water (depending on desired contraction) overnight (1 and 3% gels) or for 48 hours (5% gels). Certain hydrogel patterns (including high width co-structures for infrared thermography and patterned waved fibers for 3d bending) were bent and held in a curved shape using a safety pin. Patterns were subsequently dehydrated in ethanol for greater than 48 hours to thoroughly extract water from substrates. Finally, structures were critical point dried (at least 6 minutes at critical point, Tousimis Autosamdri) to obtain patterned nanofibrillar structures.

Example 4

The present Examples describes imaging.

Birefringence of provided constructs was achieved via polarization microscopy on an inverted microscope. Two linear polarizers (one placed at the light source, and one above provided structures) were used to eliminate direct light and illuminate birefringent material. Images were captured using a Canon DLSR camera. High-resolution images of provided structures were obtained using a Zeiss Ultra55 scanning electron microscope. Structures were removed from their respective molds, and adhered to an SEM stub (Ted Pella) using carbon tape (Ted Pella). To reveal internal morphology of provided structures, a piece of scotch tape was attached to a skin of a structure, which was subsequently peeled so as to reveal the interior. A thin layer (10 nm) of gold was finally sputtered onto substrates before imaging. Confocal images were captured using a Leica SP2 microscope. Samples were inverted within their molds above a thin coverslip (#1, Fisher), and 20 sliced images obtained through their respective depth.

Example 5

The present Example describes mechanical testing.

Mechanical tests were performed using dynamic mechanical analysis. Equivalent thickness and contraction untensed and tensed nanofibrillar fibers (initial width of 1 mm) were generated in a single test structure. Test structures were removed from their mold, and tensed and untensed portions were separated using a razor blade. Fibers were subsequently taped onto a paper scaffold for mechanical testing. Tensile testing was performed on an RSA III dynamic mechanical analysis instrument with a strain rate of 0.006 mm/s. Force-strain curves then collected and stored.

Example 6

The present Example describes Infrared Thermagraphy.

Gold-nanoparticle-doped microparticles were heated using a custom 532 nm green laser (up to 100 mW output, 3 mm spot size) and infrared thermography on provided structures was performed using an infrared camera (FLIR systems). Native—gold nanoparticle-doped aerogel constructs were removed from their respective molds, and the edges of their structures taped to an elevated platform. Samples were placed inside a tall beaker to reduce airflow, and the gold nanoparticle-doped substructure was subsequently heated with the same 532 laser to a peak temperature of around 32 C. Infrared video was subsequently taken as the incident light was removed. Eccentricity was calculated by tracking the evolution of the eccentricity of a set temperature contour over time (typically the green contour shown in FIG. 3, g).

Other embodiments are within the scope and spirit of the invention. Features implementing functions may also be physically located at various positions, including being distributed such that portions of functions are implemented at different physical locations.

Further, while the description above refers to the invention, the description may include more than one invention.

References cited in the present disclosure are all hereby incorporated by reference in their entirety for all purposes herein.

OTHER EMBODIMENTS AND EQUIVALENTS

While the present disclosure has explicitly discussed certain particular embodiments and examples of the present disclosure, those skilled in the art will appreciate that the invention is not intended to be limited to such embodiments or examples. On the contrary, the present disclosure encompasses various alternatives, modifications, and equivalents of such particular embodiments and/or example, as will be appreciated by those of skill in the art.

Accordingly, for example, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

What is claimed is:

1. An article of manufacture, comprising:
a nanofibrillar architecture, comprising: a fibrillar or fibrous material that is or comprises silk;
wherein the nanofibrillar architecture further comprises at least one additive, agent, and/or functional moiety, wherein the nanofibrillar architecture is crystalline, wherein the nanofibrillar architecture has a structure formed under a force and/or tension, wherein a comparison nanofibrillar architecture that is not crystalline and otherwise identical to the nanofibrillar architecture would be unable to maintain the structure by itself, and wherein the nanofibrillar architecture is characterized by birefringence.

2. The article of manufacture of claim 1, wherein the nanofibrillar architecture is two-dimensional.

3. The article of manufacture of claim 1, wherein the nanofibrillar architecture is three-dimensional.

4. The article of manufacture of claim 1, wherein the at least one additive, agent, and/or functional moiety is distributed throughout the nanofibrillar architecture.

5. The article of manufacture of claim 1, wherein the at least one additive, agent, and/or functional moiety is uniformly distributed throughout the nanofibrillar architecture.

6. The article of manufacture of claim 1, wherein the at least one additive, agent, and/or functional moiety is non-uniformly distributed throughout the nanofibrillar architecture.

7. The article of manufacture of claim 1, wherein the at least one additive, agent, and/or functional moiety is coated on a surface of the nanofibrillar architecture.

8. The article of manufacture of claim 1, wherein the nanofibrillar architecture forms a metashape.

9. The article of manufacture of claim 8, wherein the metashape is or comprises triangular, hexagonal, and trihexagonal cells.

10. The article of manufacture of claim 1, wherein fibrils of the nanofibrillar architectures are aligned.

11. The article of manufacture of claim 1, wherein the article further comprises anchorages, cables, or shapes.

* * * * *